United States Patent
Nakada et al.

(10) Patent No.: US 9,291,563 B2
(45) Date of Patent: Mar. 22, 2016

(54) FRET MEASUREMENT DEVICE AND FRET MEASUREMENT METHOD

(71) Applicants: Mitsui Engineering & Shipbuilding Co., Ltd., Chuo-ku, Tokyo (JP); NATIONAL UNIVERSITY CORPORATION HOKKAIDO UNIVERSITY, Sapporo-shi, Hokkaido (JP)

(72) Inventors: Shigeyuki Nakada, Tamano (JP); Yusuke Ohba, Sapporo (JP); Kyouji Doi, Tamano (JP); Yumi Asano, Tamano (JP)

(73) Assignees: MITSUI ENGINEERING & SHIPBUILDING, Tokyo (JP); NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 79 days.

(21) Appl. No.: 14/381,915

(22) PCT Filed: Mar. 22, 2013

(86) PCT No.: PCT/JP2013/058325
§ 371 (c)(1),
(2) Date: Aug. 28, 2014

(87) PCT Pub. No.: WO2013/141372
PCT Pub. Date: Sep. 26, 2013

(65) Prior Publication Data
US 2015/0044690 A1 Feb. 12, 2015

(30) Foreign Application Priority Data
Mar. 22, 2012 (JP) ................. 2012-065771

(51) Int. Cl.
*G01N 21/64* (2006.01)
*G01N 33/542* (2006.01)
*C12Q 1/68* (2006.01)

(52) U.S. Cl.
CPC .......... *G01N 21/6428* (2013.01); *C12Q 1/6818* (2013.01); *G01N 21/6408* (2013.01); *G01N 21/6458* (2013.01); *G01N 33/542* (2013.01); *G01N 2021/6441* (2013.01)

(58) Field of Classification Search
CPC .......... G01N 21/6428; G01N 21/6408; G01N 21/6458; G01N 2021/6441; C12Q 1/6818
See application file for complete search history.

(56) References Cited

U.S. PATENT DOCUMENTS

| | | | |
|---|---|---|---|
| 2002/0158212 A1* | 10/2002 | French ................ | B01L 3/50853 250/459.1 |
| 2010/0312482 A1* | 12/2010 | Nakada .............. | G01N 21/6408 702/19 |
| 2011/0284770 A1 | 11/2011 | Nakada et al. | |
| 2012/0183440 A1* | 7/2012 | Nakada .............. | G01N 15/1429 422/69 |
| 2013/0052656 A1* | 2/2013 | Hoshishima ....... | G01N 21/6428 435/7.1 |

FOREIGN PATENT DOCUMENTS

| | | |
|---|---|---|
| JP | 2007-240424 A | 9/2007 |
| WO | 2010-092784 A1 | 8/2010 |

OTHER PUBLICATIONS

International Search Report of corresponding International Application No. PCT/JP2013/058325, dated Jun. 25, 2013.

* cited by examiner

*Primary Examiner* — Christie Sung
(74) *Attorney, Agent, or Firm* — Global IP Counselors, LLP

(57) ABSTRACT

FRET measurement uses a FRET probe that includes a probe element X containing a donor fluorescent substance and a probe element Y containing an acceptor fluorescent substance and enables FRET to occur when the probe element X and the probe element Y approach to each other or bind together. The modulation frequency of laser light with which the FRET probe is irradiated is adjusted to an optimum modulation frequency that maximizes a difference between the phase difference of donor fluorescence emitted from the donor fluorescent substance with respect to intensity modulation of the laser light at the time when FRET occurs and the phase difference of donor fluorescence emitted from the donor fluorescent substance with respect to intensity modulation of the laser light at the time when FRET does not occur.

12 Claims, 9 Drawing Sheets

|  | FIRST FLUORESCENT COMPONENT | | SECOND FLUORESCENT COMPONENT | |
| --- | --- | --- | --- | --- |
|  | $\alpha_1$ | $\tau_1$(nsec) | $\alpha_2$ | $\tau_2$(nsec) |
| AT TIME OF NON-FRET | 0.5 | 3.0 | 0.5 | 1.0 |
| AT TIME OF OCCURRENCE OF FRET | 0.2 | 3.0 | 0.8 | 0.3 (FRET OCCURS) |

FRET MEASUREMENT DEVICE AND FRET MEASUREMENT METHOD

TECHNICAL FIELD

The present invention relates to a device and method for measuring FRET using a FRET probe that includes a probe element X containing a donor fluorescent substance and a probe element Y containing an acceptor fluorescent substance and enables fluorescence resonance energy transfer (FRET) to occur when the probe element X and the probe element Y approach to each other or bind together.

BACKGROUND ART

At present, functional analysis of proteins has become important as post-genome-related technology in medical care, drug development, and food industry. Particularly, in order to analyze cellular action, it is necessary to investigate interaction (binding, separation) between a protein as a biological substance and another protein or a low-molecular compound in a living cell.

The interaction between a protein as a biological substance and another protein or a low-molecular compound in a living cell is analyzed by utilizing a fluorescence resonance energy transfer (FRET) phenomenon. Interaction between molecules in a region of several nanometers can be measured by measuring fluorescence generated by the FRET phenomenon. FRET refers to a phenomenon in which, when a donor fluorescent substance is excited by laser light irradiation, part of excitation energy is transferred to an acceptor fluorescent substance located close to the donor fluorescent substance without emitting fluorescence so that the acceptor fluorescent substance emits fluorescence.

When the presence or absence of the occurrence of FRET is investigated by giving a fluorescent substance to a biological substance such as a protein, a method is conventionally used in which the presence or absence of the occurrence of FRET is investigated based on a change in the intensity of fluorescence emitted from the fluorescent substance irradiated with laser light. More specifically, this method measures the decrement of the fluorescence intensity of donor fluorescence emitted from a donor fluorescent substance due to the transfer of part of excitation energy from the donor fluorescent substance and the increment of fluorescence intensity due to emission of acceptor fluorescence from an acceptor fluorescent substance using the transferred excitation energy. However, this method cannot always accurately judge the presence or absence of the occurrence of FRET because the decrement and the increment vary depending on the amount of the donor fluorescent substance or the acceptor fluorescent substance (label) contained in a measuring object.

On the other hand, as a method less likely to be influenced by the amount of a label, such as a donor fluorescent substance or an acceptor fluorescent substance, contained in a measuring object, a method is known in which the fluorescence lifetime of donor fluorescence emitted from a donor fluorescent substance is measured, and the presence or absence of the occurrence of FRET is judged based on a change in the fluorescence lifetime (Patent Literature 1).

CITATION LIST

Patent Literature

Patent Literature 1: JP 2007-240424 A

SUMMARY OF INVENTION

Technical Problem

The above method can more accurately judge the presence or absence of the occurrence of FRET by using a change in fluorescence lifetime as well as the decrement of the fluorescence intensity of donor fluorescence and the increment of the fluorescence intensity of acceptor fluorescence. When the donor fluorescent substance emits one kind of donor fluorescence (fluorescence lifetimes are the same), the method can accurately detect a change in fluorescence lifetime and therefore can judge the presence or absence of the occurrence of FRET. However, when the donor fluorescent substance emits donor fluorescence containing a plurality of fluorescent components different in fluorescence lifetime, the method sometimes cannot accurately judge the presence or absence of the occurrence of FRET. Particularly, when a biological substance or the like is an object to be measured, a fluorescent protein is used as a label such as a donor fluorescent substance or an acceptor fluorescent substance. However, some fluorescent proteins emit two or more kinds of fluorescent components, i.e., two or more kinds of fluorescent components different in fluorescence lifetime, and therefore the method sometimes cannot accurately judge the presence or absence of the occurrence of FRET when a fluorescent protein is used as a donor fluorescent substance.

It is therefore an object of the present invention to provide a FRET measurement device and a FRET measurement method that can accurately judge the presence or absence of the occurrence of FRET.

Means to Solve the Problem

An aspect of the invention is a FRET measurement device. The device includes:

a conduit through which a test sample flows, the test sample including: a FRET probe that includes a probe element X labeled with a donor fluorescent substance and a probe element Y labeled with an acceptor fluorescent substance and enables FRET to occur when the probe element X and the probe element Y approach to each other or bind together; and a test object about which it is unknown whether or not it has a approaching/binding property of allowing the probe element X and the probe element Y to approach to each other or bind together or a separating property of separating the probe element X and the probe element Y that are in a state where they adjoin each other or bind together;

a light source unit configured to emit, toward the conduit, laser light whose intensity is modulated using a modulation signal;

a light-receiving unit configured to receive fluorescence emitted from the FRET probe in the test sample by irradiation with the intensity-modulated laser light and outputs a fluorescent signal; and an analyzing unit configured to:

determine, using the fluorescent signal and the modulation signal, a phase difference of donor fluorescence emitted from the donor fluorescent substance with respect to the modulation signal as a first phase difference;

further determine a fluorescence intensity of donor fluorescence emitted from the donor fluorescent substance and a fluorescence intensity of acceptor fluorescence emitted from the acceptor fluorescent substance; and judge, using a fluorescence lifetime of the donor fluorescence obtained from the determined first phase difference, the fluorescence intensity of donor fluorescence, and the fluorescence intensity of acceptor fluorescence, whether or not the test object has the approaching/binding property or the separating property.

A modulation frequency used for the modulation signal in the light source unit is an optimum modulation frequency that maximizes a difference between a second phase difference of donor fluorescence emitted from the donor fluorescent substance with respect to the modulation signal at a time when the FRET occurs and a third phase difference of donor fluorescence emitted from the donor fluorescent substance with respect to the modulation signal at a time when the FRET does not occur.

Preferably, the FRET measurement device further includes a frequency adjusting unit configured to adjust the modulation frequency.

Then, the frequency adjusting unit is configured to determine, as the second phase difference, a phase difference of donor fluorescence emitted from the donor fluorescent substance with respect to the modulation signal, by using a positive control sample containing the FRET probe whose probe element X and probe element Y are allowed to approach to each other or bind together instead of the test sample through the conduit, the light source unit, the light-receiving unit, and the analyzing unit while the modulation frequency is changed.

The frequency adjusting unit is further configured to determine, as the third phase difference, a phase difference of donor fluorescence emitted from the donor fluorescent substance with respect to the modulation signal, by using a negative control sample containing the FRET probe whose probe element X and probe element Y are not allowed to approach to each other or bind together instead of the test sample through the conduit, the light source unit, the light-receiving unit, and the analyzing unit while the modulation frequency is changed.

The frequency adjusting unit is configured to find out the optimum modulation frequency based on a difference between the second phase difference and the third phase difference.

The positive control sample is used as each of samples of a FRET sample group that enables FRET occurrence to determine the second phase difference or a fluorescence lifetime $\tau_{FRET}$ obtained from the second phase difference and then to determine an average Ave1 and standard deviation Sd1 of the second phase difference or fluorescence lifetime $\tau_{FRET}$ of the FRET sample group, and the negative control sample is used as each of samples of a NON-FRET sample group that does not allow FRET occurrence, to determine the third phase difference or a fluorescence lifetime $\tau_{NON-FRET}$ obtained from the third phase difference and then to determine an average Ave2 and standard deviation Sd2 of the third phase difference or fluorescence lifetime $\tau_{NON-FRET}$ of the NON-FRET sample group.

Then, a value Z defined by the following formula at the optimum modulation frequency is preferably more than 0 but less than 1:

$$Z=1-3\cdot(Sd1+Sd2)/|Ave1-Ave2|.$$

The donor fluorescent substance emits, for example, two or more kinds of fluorescent components, each having known values of a fluorescence parameter including information about fluorescence lifetime and fluorescence intensity. Then, preferably, the FRET measurement device further includes a frequency adjusting unit configured to adjust the modulation frequency.

The frequency adjusting unit is configured to:
perform a simulation calculation using the values of the fluorescence parameter while changing the modulation frequency to determine the second phase difference and third phase difference of the donor fluorescence with respect to the modulation signal; and
find out the optimum modulation frequency based on a result of the simulation calculation.

The values of the fluorescence parameter are preferably identified using fluorescence lifetime imaging microscopy.

The analyzing unit preferably performs the process as described below. The analyzing unit is configured to previously acquire, using the FRET probe, a range in which a fluorescence lifetime $\tau_{FRET}$ of donor fluorescence emitted from the donor fluorescent substance can take values at a time when the FRET occurs, a range in which a fluorescence lifetime $\tau_{NON-FRET}$ of the donor fluorescence emitted from the donor fluorescent substance can take values at a time when the FRET does not occur, a range in which a ratio $R_{FRET}$ of fluorescence intensity of acceptor fluorescence emitted from the acceptor fluorescent substance to fluorescence intensity of donor fluorescence emitted from the donor fluorescent substance can take values at a time when the FRET occurs, and a range in which a ratio $R_{NON-FRET}$ of fluorescence intensity of acceptor fluorescence emitted from the acceptor fluorescent substance to fluorescence intensity of donor fluorescence emitted from the donor fluorescent substance can take values at a time when the FRET does not occur.

The analyzing unit is configured to:
calculate, using the first phase difference determined using the test sample and the optimum modulation frequency, a fluorescence lifetime $\tau_{sample}$ of donor fluorescence emitted from the donor fluorescent substance, and further calculate a ratio $R_{sample}$ of fluorescence intensity of acceptor fluorescence emitted from the acceptor fluorescent substance to fluorescence intensity of donor fluorescence emitted from the donor fluorescent substance; and
judge, from the calculated fluorescence lifetime $\tau_{sample}$ and fluorescence intensity ratio $R_{sample}$, whether or not the test object has the approaching/binding property or the separating property based on the range in which the fluorescence lifetime $\tau_{FRET}$ can take values, the range in which the fluorescence lifetime $\tau_{NON-FRET}$ can take values, the range in which the ratio $R_{FRET}$ can take values, and the range in which the ratio $R_{NON-FRET}$ can take values.

The analyzing unit is configured to:
determine, as the second phase difference, a phase difference of donor fluorescence emitted from the donor fluorescent substance with respect to the modulation signal, by using a positive control sample containing the FRET probe whose probe element X and probe element Y are allowed to approach to each other or bind together instead of the test sample through the conduit, the light source unit, the light-receiving unit, and the analyzing unit, and to obtain, from the second phase difference and the modulation frequency, a plurality of values of the fluorescence lifetime $\tau_{FRET}$ of donor fluorescence emitted from the donor fluorescent substance at a time when the FRET occurs;

determines a plurality of values of the ratio $R_{FRET}$ from a fluorescence intensity of donor fluorescence emitted from the donor fluorescent substance and a fluorescence intensity of acceptor fluorescence emitted from the acceptor fluorescent substance, by using the positive control sample instead of the test sample through the conduit, the light source unit, the light-receiving unit; and determine the range in which the fluorescence lifetime $\tau_{FRET}$ can take values and the range in which the ratio $R_{FRET}$ can take values.

The analyzing unit is configured to:

determine, as the third phase difference, a phase difference of donor fluorescence emitted from the donor fluorescent substance with respect to the modulation signal, by using a negative control sample containing the FRET probe whose probe element X and probe element Y are not allowed to approach to each other or bind together instead of the test sample through the conduit, the light source unit, the light-receiving unit, to obtain, from the third phase difference and the modulation frequency, a plurality of values of the fluorescence relaxation lifetime $\tau_{NON-FRET}$ of donor fluorescence emitted from the donor fluorescent substance at a time when the FRET does not occur; and further determine a plurality of values of the ratio $R_{NON-FRET}$ from a fluorescence intensity of the donor fluorescence and a fluorescence intensity of acceptor fluorescence emitted from the acceptor fluorescent substance, by using the negative control sample instead of the test sample through the conduit, the light source unit, the light-receiving unit, and determine the range in which the fluorescence lifetime $\tau_{NON-FRET}$ can take values and the range in which the ratio $R_{NON-FRET}$ can take values.

Another aspect of the invention is a FRET measurement method using a device including a conduit, a light source unit, a light-receiving unit, and an analyzing unit. The method includes the steps of:

flowing, through the conduit, a test sample comprising: a FRET probe that comprises a probe element X containing a donor fluorescent substance and a probe element Y containing an acceptor fluorescent substance and enables FRET to occur when the probe element X and the probe element Y approach to each other or bind together; and a test object about which it is unknown whether or not it has a property of allowing the probe element X and the probe element Y to approach to each other or bind together or a property of separating from each other the probe element X and the probe element Y that are in a state where they adjoin each other or bind together;

causing the light source unit to emit laser light whose intensity is modulated using a modulation signal toward the conduit;

causing the light-receiving unit to receive fluorescence emitted from the FRET probe in the test sample by irradiation with the intensity-modulated laser light and output a fluorescent signal; and causing the analyzing unit to determine, using the fluorescent signal and the modulation signal, a phase difference of donor fluorescence emitted from the donor fluorescent substance with respect to the modulation signal as a first phase difference, further to determine a fluorescence intensity of donor fluorescence emitted from the donor fluorescent substance and a fluorescence intensity of acceptor fluorescence emitted from the acceptor fluorescent substance, and then to judge, using a fluorescence lifetime of the donor fluorescence obtained from the determined first phase difference, the fluorescence intensity of donor fluorescence, and the fluorescence intensity of acceptor fluorescence, whether or not the test object has a property of allowing the probe element X and the probe element Y to approach to each other or bind together or a property of separating the probe element X and the probe element Y from each other.

A modulation frequency used for the modulation signal for intensity modulation of the laser light is adjusted to an optimum modulation frequency that maximizes a difference between a second phase difference of donor fluorescence emitted from the donor fluorescent substance with respect to the modulation signal at a time when the FRET occurs and a third phase difference of donor fluorescence emitted from the donor fluorescent substance with respect to the modulation signal at a time when the FRET does not occur.

Preferably, the FRET measurement method further includes the step of adjusting the modulation frequency.

When the modulation frequency is adjusted, a phase difference of donor fluorescence emitted from the donor fluorescent substance with respect to the modulation signal is determined as the second phase difference, by using a positive control sample containing the FRET probe whose probe element X and probe element Y are allowed to approach to each other or bind together instead of the test sample through the conduit, the light source unit, the light-receiving unit, and the analyzing unit while the Modulation frequency is changed, a phase difference of donor fluorescence emitted from the donor fluorescent substance with respect to the modulation signal is further determined as the third phase difference, by using a negative control sample containing the FRET probe whose probe element X and probe element Y are not allowed to approach to each other or bind together instead of the test sample through the conduit, the light source unit, the light-receiving unit, and the analyzing unit while the modulation frequency is changed, and the optimum modulation frequency is found out based on a difference between the second phase difference and the third phase difference.

At this time, the second phase difference or a fluorescence lifetime $\tau_{FRET}$ obtained from the second phase difference is determined using the positive control sample as each of samples of a FRET sample group that enables FRET to occur, so that an average Ave1 and standard deviation Sd1 of the second phase difference or fluorescence lifetime $\tau_{FRET}$ of the FRET sample group are determined, and the third phase difference or a fluorescence lifetime $\tau_{NON-FRET}$ obtained from the third phase difference is further determined using the negative control sample as each of samples of a NON-FRET sample group that does not allow FRET to occur, so that an average Ave2 and standard deviation Sd2 of the third phase difference or fluorescence lifetime $\tau_{NON-FRET}$ of the NON-FRET sample group are determined.

Then, a value Z defined by the following formula at the optimum modulation frequency is preferably more than 0 but less than 1.

$$Z=1-3\cdot(Sd1+Sd2)/|Ave1-Ave2|.$$

In a case that the donor fluorescent substance emits two or more kinds of fluorescent components, each having known values of a fluorescence parameter including information about fluorescence lifetime and fluorescence intensity, the FRET measurement method further includes the step of adjusting the modulation frequency. When the modulation frequency is adjusted, a simulation calculation is preferably performed using the values of the fluorescence parameter while the modulation frequency is changed, to determine the second phase difference and third phase difference of the donor fluorescence with respect to the modulation signal, and the optimum modulation frequency is preferably found out based on a result of the simulation calculation.

Then, the values of the fluorescence parameter are preferably identified using fluorescence lifetime imaging microscopy.

Advantageous Effects of Invention

The above-described FRET measurement device and FRET measurement method can accurately judge the presence or absence of the occurrence of FRET.

DESCRIPTION OF EMBODIMENTS

Figure 1A:
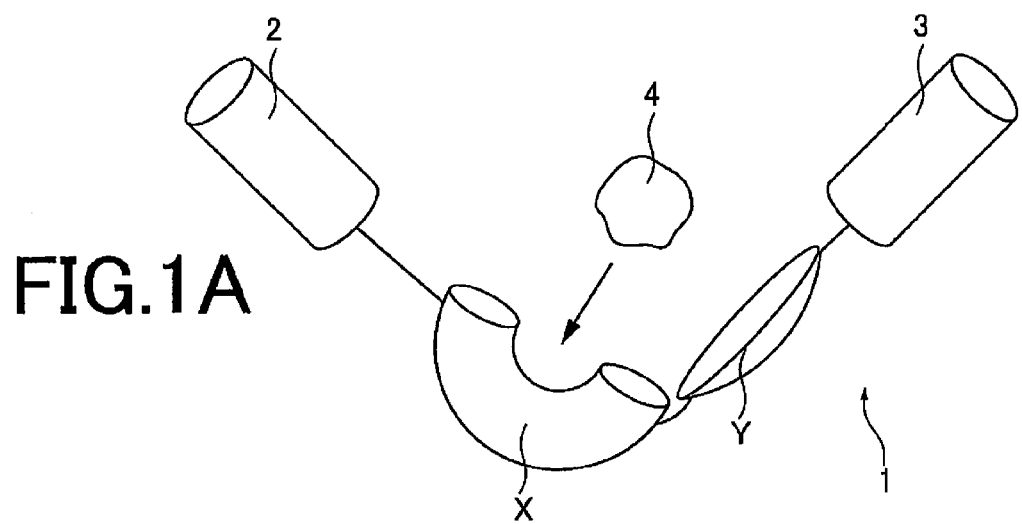
FIGS. 1A to 1C are diagrams that illustrate various states of a measuring probe.

Hereinbelow, a FRET measurement device and a FRET measurement method according to the present invention will be described in detail.

<Measuring Probe>

A measuring probe used in this embodiment is a probe for use in a flow cytometer 10 that will be described later as one embodiment of the FRET measurement device. This measuring probe is a FRET probe including a probe element X labeled with a donor fluorescent substance and a probe element Y labeled with an acceptor fluorescent substance. FRET occurs when the probe element X and the probe element Y approach to each other (or bind together) so that the donor fluorescent substance and the acceptor fluorescent substance are located close to each other (e.g., when the donor fluorescent substance and the acceptor fluorescent substance are located within a range of several nanometers). The flow cytometer 10 according to this embodiment uses a test sample containing this FRET probe as well as a test object (e.g., a drug) to judge the presence or absence of the occurrence of FRET. As the test sample, a biological cell incorporating the measuring probe and the test object is exemplified. The test sample may be a suspension liquid directly containing the measuring probe and the test object therein without incorporating them into biological cells.

The use of this measuring probe makes it possible to determine whether or not the test object has the property of allowing the probe element X and the probe element Y to approach to each other (or bind together) (hereinafter, referred to as "approaching/binding property") or the property of separating (hereinafter, referred to as "separating property") from each other the probe element X and the probe element Y that are in a state where they adjoin each other (or bind together). For example, it is possible to determine whether a drug has the property of inducing the approach (or binding) of the probe element X and the probe element Y to each other (approaching/binding property) or the property of inhibiting the approach (or binding) of the probe element X and the probe element Y to each other (separating property). Further, it is possible to determine, inside a biological cell, whether action between the test probe and the test object incorporated into the biological cell, e.g., cell nucleus, is strong or weak. Further, it is also possible to determine whether or not action between the test probe and the test object changes due to a change in the environment of a biological cell or due to production of a certain substance in a biological cell, e.g., cell nucleus.

It is to be noted that, in this embodiment, the probe element X and the probe element Y that form one probe body may be two separate elements, or part of one probe body may be formed from the probe element X and the probe element Y. When part of one probe body is formed from the probe element X and the probe element Y and the one probe body is deformed into a folded shape by increasing its bending angle, the probe element X and the probe element Y approach to each other (or bind together). When the one probe body being in a folded state is deformed so that its bending angle reduces, the probe element X and the probe element Y are separated from each other.

Figure 1B:
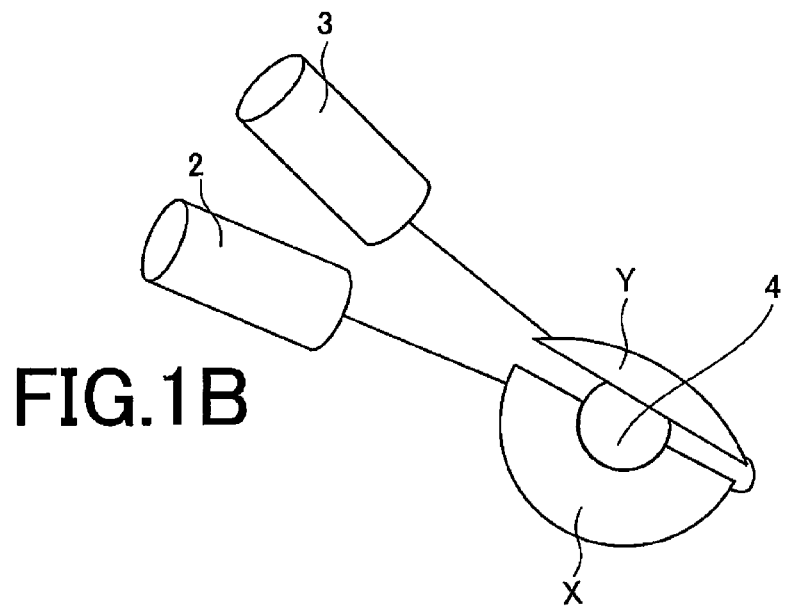
Figure 1C:
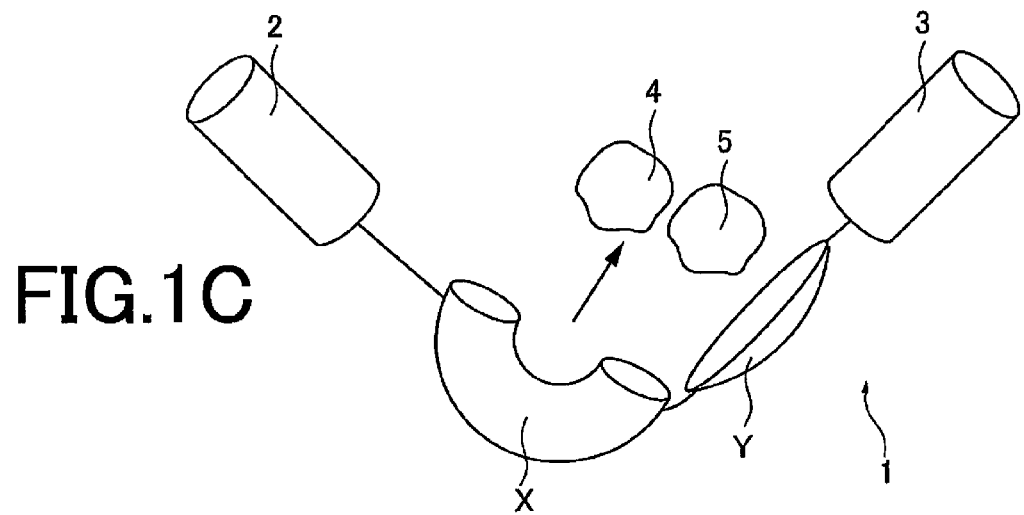

FIGS. 1A to 1C are diagrams that illustrate various states of a measuring probe 1. The measuring probe 1 includes a probe element X labeled with a donor fluorescent substance 2 and a probe element Y labeled with an acceptor fluorescent substance 3.

FIG. 1A illustrates a state where the probe element X labeled with the donor fluorescent substance 2 and the probe element Y labeled with the acceptor fluorescent substance 3 are separated from each other. When a test object 4 is given in this state, as illustrated in FIG. 1B, the probe element X and the probe element Y approach to each other (or bind together) so that the donor fluorescent substance 2 and the acceptor fluorescent substance 3 are located close to each other to the extent that FRET occurs. Further, when another test object 5 is given in the state illustrated in FIG. 1B, the labeled probe element X and the probe element Y labeled with the acceptor fluorescent substance Y are separated from each other to the extent that FRET does not occur between the donor fluorescent substance 2 and the acceptor fluorescent substance 3. The FRET measurement device according to this embodiment uses, as an object to be tested, a test object, such as the test object 4 or 5, about which it is unknown whether it has the property of allowing the probe element X and the probe element Y to approach to each other (or bind together) (approaching/binding property) or the property of separating from each other the probe element X and the probe element Y (separating property) that are in a state where they adjoin each other (or bind together). FRET is, of course, caused by irradiation of the donor fluorescent substance 2 with laser light.

In FIGS. 1A to 1C, the probe element X and the probe element Y are linked to and labeled with the donor fluorescent substance 2 and the acceptor fluorescent substance 3, respectively. However, a linking method is not particularly limited, and the donor fluorescent substance 2 and the acceptor fluorescent substance 3 may be labeled by any method.

Figure 2:
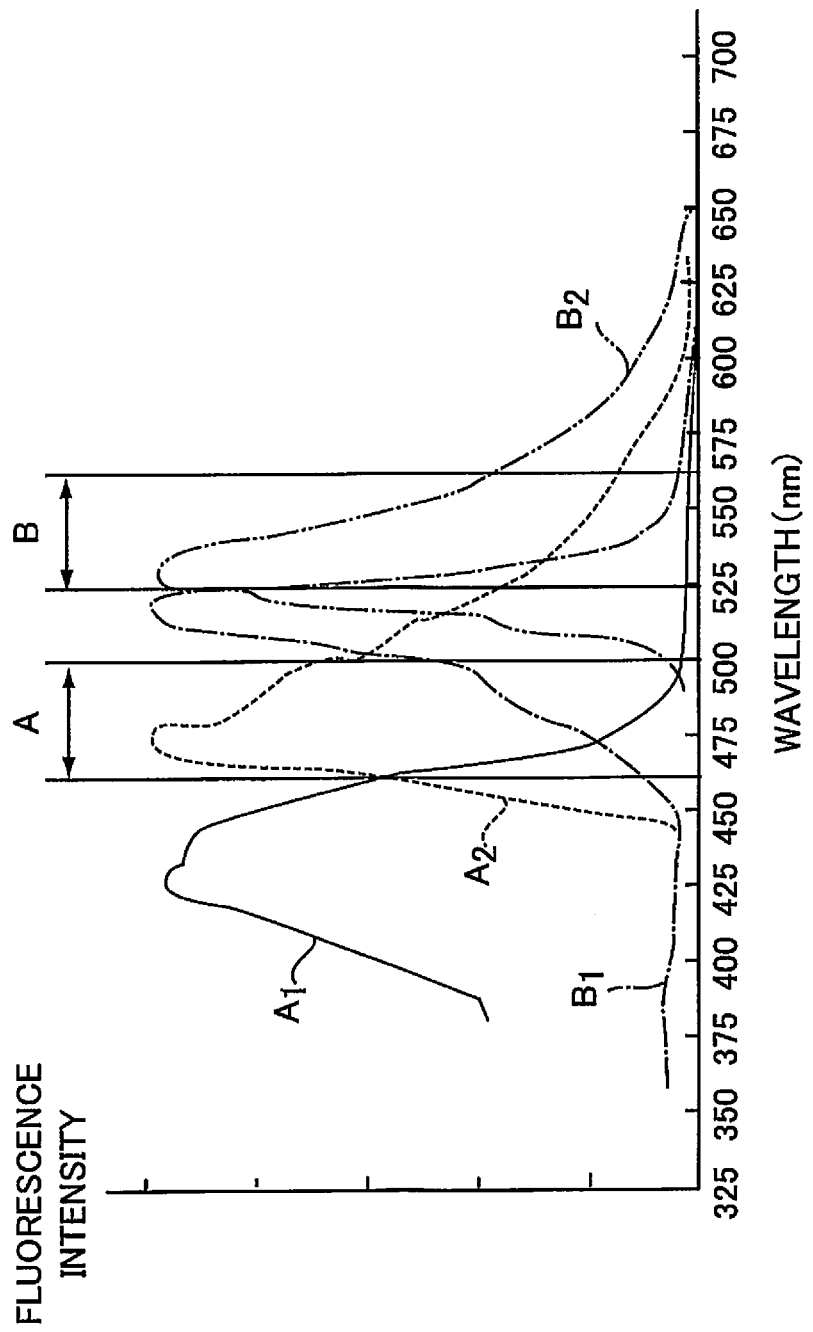
FIG. 2 is a diagram that illustrates examples of energy absorption spectra and fluorescence emission spectra of a donor fluorescent substance and an acceptor fluorescent substance of the measuring probe illustrated in FIG. 1.

FIG. 2 is a diagram that illustrates examples of energy absorption spectra and fluorescence emission spectra of the donor fluorescent substance 2 and the acceptor fluorescent substance 3. As the donor fluorescent substance 2, for example, CFP (Cyan Fluorescent Protein) may be used. As the acceptor fluorescent substance 3, for example, YFP (Yellow Fluorescent Protein) may be used.

A curve $A_1$ represents one example of the energy absorption spectrum of the donor fluorescent substance 2, and a curve $A_2$ represents one example of the fluorescence emission spectrum of the donor fluorescent substance 2. A curve $B_1$ represents one example of the energy absorption spectrum of the acceptor fluorescent substance 3, and a curve $B_2$ represents one example of the fluorescence emission spectrum of the acceptor fluorescent substance 3.

As illustrated in FIG. 2, a wavelength range in which the donor fluorescent substance 2 mainly absorbs energy is 405 nm to 450 nm, and a wavelength range in which the acceptor fluorescent substance 3 mainly absorbs energy is 470 nm to 530 nm.

In general, when the distance between the donor fluorescent substance 2 and the acceptor fluorescent substance 3 is 2 nm or less, part of energy absorbed by the donor fluorescent substance 2 irradiated with laser light is transferred to the acceptor fluorescent substance 3 by coulomb interaction. The acceptor fluorescent substance 3 is excited by absorption of the energy transferred from the donor fluorescent substance 2 by coulomb interaction and emits fluorescence. This phenomenon is fluorescence resonance energy transfer (FRET). In this case, from the viewpoint of occurrence of strong FRET, an overlap in wavelength range between the curve $A_2$ representing the fluorescence emission spectrum of the donor fluorescent substance 2 and the curve $B_1$ representing the energy absorption spectrum of the acceptor fluorescent substance 3 is preferably wide.

When such a measuring probe 1 is used, the modulation frequency of a modulation signal used to modulate the intensity of laser light used in the flow cytometer 10 that will be described later is set to an optimum modulation frequency that maximizes a difference between a second phase difference that will be described later and a third phase difference that will be described later. The second phase difference is the phase difference of donor fluorescence with respect to the modulation signal at the time when FRET occurs in the measuring probe 1. The third phase difference is the phase difference of donor fluorescence with respect to the modulation signal at the time when FRET does not occur in the measuring probe 1. Therefore, the flow cytometer 10 can accurately judge the presence or absence of the occurrence of FRET. In the following description, fluorescence emitted from the donor fluorescent substance 2 is referred to as donor fluorescence, and fluorescence emitted from the acceptor fluorescent substance 2 is referred to as acceptor fluorescence.

<FRET Measurement Device>

Figure 3:
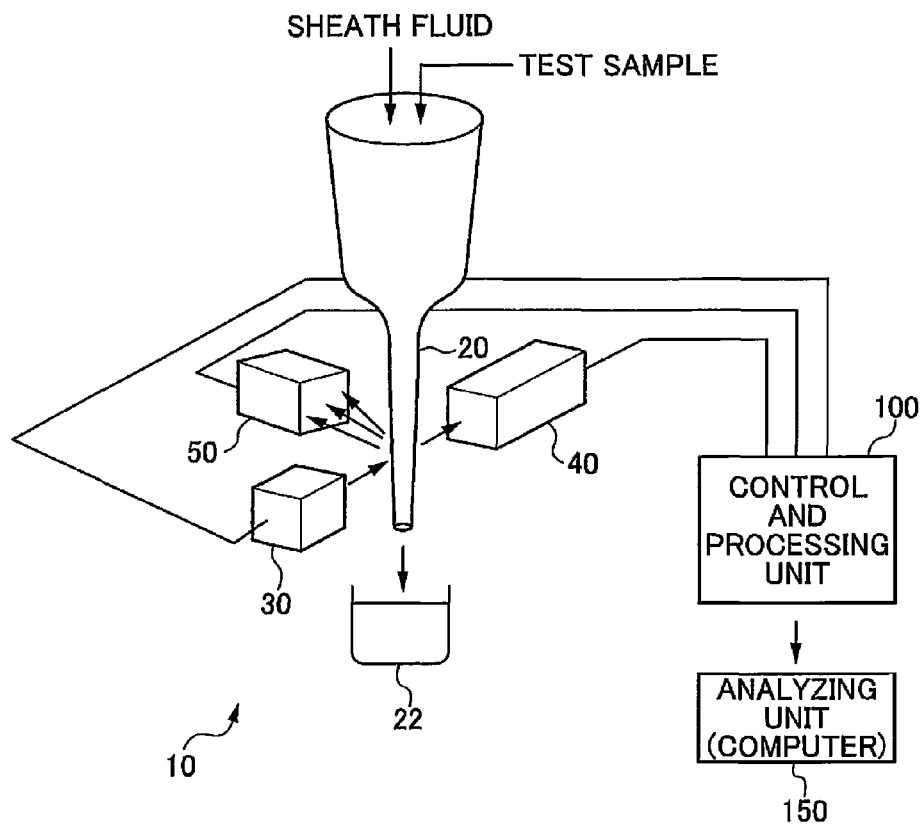
FIG. 3 is a schematic configuration diagram of a flow cytometer that is one embodiment of a FRET measurement device according to the present invention.

FIG. 3 is a schematic configuration diagram of the flow cytometer 10 that is one embodiment of the FRET measurement device according to the present invention.

The flow cytometer 10 according to this embodiment irradiates a test sample containing, for example, the measuring probe 1 and the test object 5 with laser light, and measures fluorescence emitted from the measuring probe 1 in the test sample. The flow cytometer 10 uses a measured fluorescent signal to judge FRET.

As illustrated in FIG. 3, the flow cytometer 10 includes a conduit 20, a light source unit 30, light-receiving units 40 and 50, a control and processing unit 100, and an analyzing unit 150.

The conduit 20 allows a sheath fluid forming a high-speed flow and a test sample to flow through it at the same time. In the conduit 20, a laminar sheath flow is formed in which the test sample containing the measuring probe 1 flows in line. In the middle of the conduit 20, there is a laser light irradiation point as a measuring point. At this measuring point, the test sample containing the measuring probe 1 sequentially emits fluorescence by irradiation with laser light. At the exit of the conduit 20, a collection container 22 is provided to collect the test sample.

The flow cytometer 10 judges whether or not the measuring probe 1 contained in the test sample has changed to a state where, as illustrated in FIG. 1C, the probe element X and the probe element Y are separated from each other so that FRET does not occur between the donor fluorescent substance 2 and the acceptor fluorescent substance 3 when the test object 5 has been given to the measuring probe 1 being in a state where, as illustrated in FIG. 1B, the probe element X and the probe element Y adjoin each other (or bind together) so that the donor fluorescent substance 2 and the acceptor fluorescent substance 3 are located close to each other (i.e., in a state where FRET occurs).

Although no description will be given, the flow cytometer 10 may also judge whether the measuring probe 1 has changed to a state where, as illustrated in FIG. 1B, the probe element X and the probe element Y adjoin each other (or bind together) so that FRET occurs between the donor fluorescent substance 2 and the acceptor fluorescent substance 3 located close to each other when the test object 4 has been given in a state where, as illustrated in FIG. 1A, the probe element X and the probe element Y are separated from each other.

The light source unit 30 irradiates the measuring probe 1 passing through the measuring point in the conduit 20 with laser light whose intensity is modulated using a modulation signal. When the measuring probe 1 is irradiated with the laser light, the donor fluorescent substance 2 mainly absorbs energy. For example, when the donor fluorescent substance 2 is CFP (Cyan Fluorescent Protein) and the acceptor fluorescent substance 3 is YFP (Yellow Fluorescent Protein), laser light having a wavelength of 405 nm to 450 nm is used at which the donor fluorescent substance 2 mainly absorbs energy. The light source unit 30 includes, for example, a semiconductor laser. The laser light emitted from the light source unit 30 has an output power of, for example, 5 mW to 100 mW. The measuring probe 1 irradiated with the laser light emitted from the light source unit 30 emits fluorescence, and the fluorescence is received by the light-receiving unit 50.

The light-receiving unit 40 is arranged so as to face the light source unit 30 across the conduit 20. The light-receiving unit 40 includes a photoelectric converter that outputs a detection signal indicating the passage of the measuring probe 1 through the measuring point when the measuring probe 1 passing through the measuring point scatters the laser light. The signal outputted by the light-receiving unit 40 is supplied to the control and processing unit 100. The signal supplied from the light-receiving unit 40 to the control and processing unit 100 is used as a trigger signal that announces the timing at which the measuring probe 1 passes through the measuring point in the conduit 20 and allows the control and processing unit 100 to start processing and control.

The light-receiving unit 50 is arranged on the line of intersection of a plane that passes through the measuring point and is orthogonal to the direction in which the laser light emitted from the light source unit 30 travels and a plane that passes through the measuring point and is orthogonal to the direction in which the measuring probe 1 in the conduit 20 moves. The light-receiving unit 50 includes photoelectric converters, such as photomultiplier tubes or avalanche photodiodes, that receive fluorescence emitted from the measuring probe 1 irradiated with the laser light at the measuring point.

Figure 4:
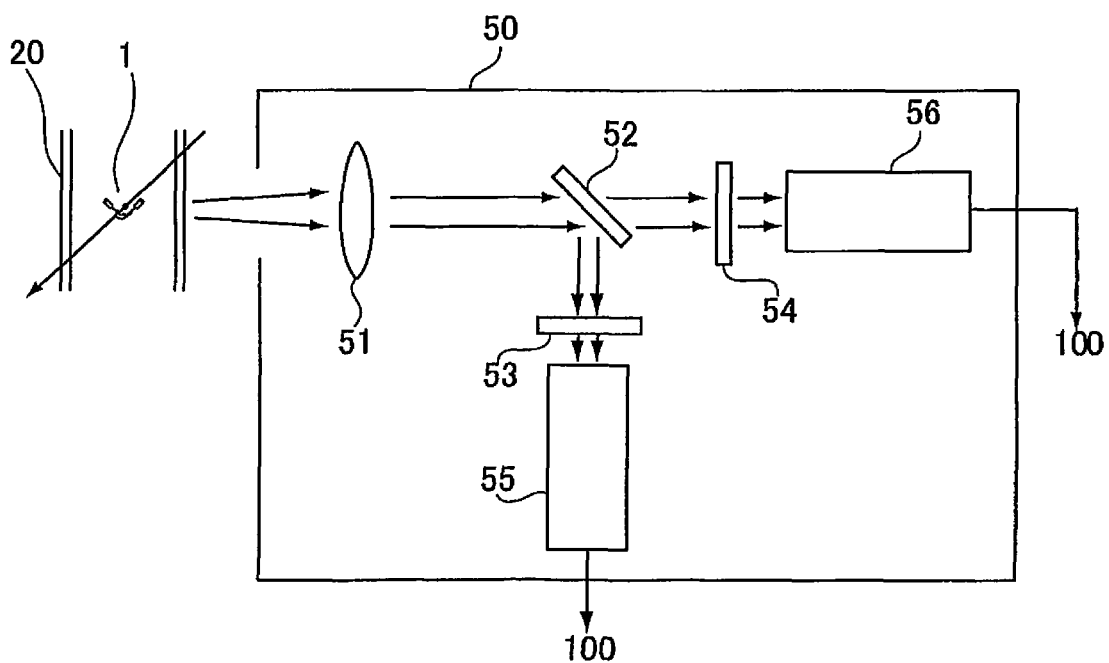
FIG. 4 is a schematic configuration diagram that illustrates one example of a light-receiving unit of this embodiment.

FIG. 4 is a schematic configuration diagram that illustrates one example of the light-receiving unit 50 of this embodiment. As illustrated in FIG. 4, the light-receiving unit 50 includes a lens system 51, a dichroic mirror 52, band-pass filters 53 and 54, and photoelectric converters 55 and 56.

The lens system 51 focuses fluorescence emitted from the measuring probe 1. The dichroic mirror 52 is configured to have such reflection and transmission wavelength characteristics that fluorescence emitted from the acceptor fluorescent substance 3 is transmitted and fluorescence emitted from the donor fluorescent substance 2 is reflected.

The band-pass filters 53 and 54 are provided in front of the light-receiving surfaces of the photoelectric converters 55 and 56. The band-pass filters 53 and 54 transmit only fluorescence in a predetermined wavelength band. More specifically, the band-pass filter 53 is configured to transmit light in the wavelength band of donor fluorescence emitted from the donor fluorescent substance 2 (i.e., in a band denoted by A in FIG. 2). The band-pass filter 54 is configured to transmit light in the wavelength band of acceptor fluorescence emitted from the acceptor fluorescent substance 3 (i.e., in a band denoted by B in FIG. 2).

The photoelectric converters 55 and 56 convert received light to an electric signal. Each of the photoelectric converters 55 and 56 is, for example, a sensor equipped with a photomultiplier tube. The fluorescence received by the photoelectric converters 55 and 56 fluctuates in intensity and has a phase delay with respect to the intensity-modulated laser light due to the fluorescence emission process of the donor fluorescent substance 2 and the acceptor fluorescent substance 3. Therefore, each of the photoelectric converters 55 and 56 receives an optical signal having information about a phase difference with respect to the intensity-modulated laser light, and converts the optical signal to an electric signal. The signals outputted by the photoelectric converters 55 and 56, that is, fluorescent signals are supplied to the control and processing unit 100.

Figure 5:
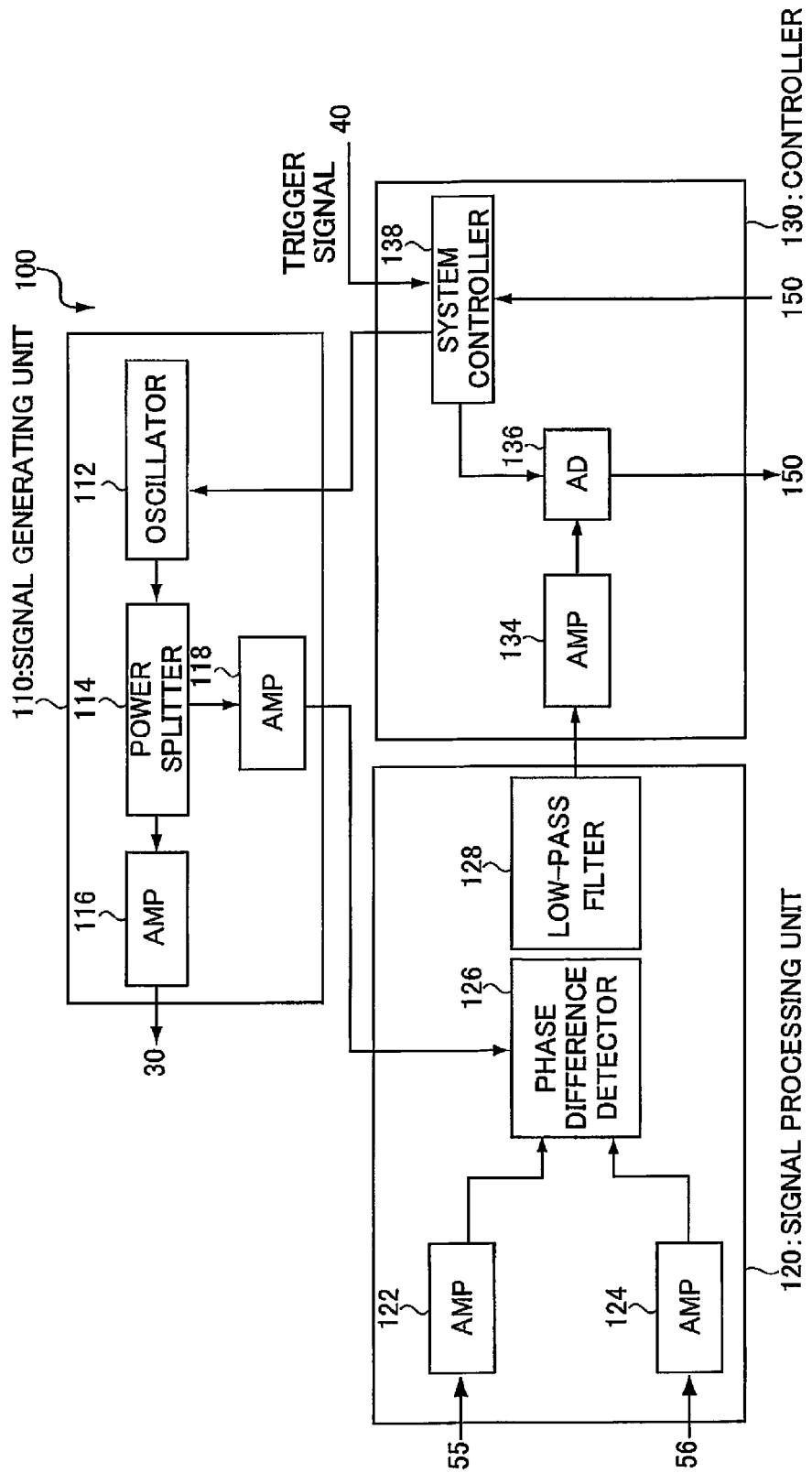
FIG. 5 is a schematic configuration diagram that illustrates one example of a control and processing unit of this embodiment.

FIG. 5 is a schematic configuration diagram that illustrates one example of the control and processing unit 100 of this embodiment. As illustrated in FIG. 5, the control and processing unit 100 includes a signal generating unit 110, a signal processing unit 120, and a controller 130.

The signal generating unit 110 generates a modulation signal for time-modulating the intensity of the laser light. The modulation signal is, for example, a sinusoidal signal having a predetermined frequency, and the predetermined frequency is set to fall in the range of, for example, 10 MHz to 400 MHz.

The signal generating unit 110 includes an oscillator 112, a power splitter 114, and amplifiers 116 and 118. The modulation signal generated by the oscillator 112 is split by the power splitter 114 and then supplied to the light source unit 30 and the signal processing unit 120. The reason why the signal generating unit 110 supplies the modulation signal to the signal processing unit 120 is that, as will be described later, the modulation signal is used as a reference signal for determining the phase difference of donor fluorescence emitted from the donor fluorescent substance 2 with respect to the modulation signal, more specifically the phase difference of the fluorescent signal with respect to the modulation signal.

Further, the modulation signal is used as a signal for modulating the amplitude of the laser light emitted from the light source unit 30.

The processing unit 120 uses the fluorescent signal and the modulation signal to determine information about the phase difference of donor fluorescence emitted from the measuring probe 1 with respect to the modulation signal (first phase difference). The signal processing unit 120 includes amplifiers 122 and 124, a phase difference detector 126, and a low-pass filter 128.

The amplifiers 122 and 124 amplify the signals outputted by the photoelectric converters 55 and 56, and output the amplified signals to the phase difference detector 126.

The phase difference detector 126 detects the phase difference of each of the fluorescent signals of donor fluorescence and acceptor fluorescence outputted by the photoelectric converters 55 and 56 with respect to the modulation signal (reference signal). The phase difference detector 126 has an IQ mixer not illustrated. The IQ mixer multiplies the reference signal and the fluorescent signal to calculate a processed signal containing a cos component (real part) of the fluorescent signal and a high-frequency component. Further, the IQ mixer multiplies a signal obtained by shifting the phase of the reference signal by 90 degrees and the fluorescent signal to calculate a processed signal containing a sin component (imaginary part) of the fluorescent signal and a high-frequency component.

The low-pass filter 128 removes the high-frequency component from the signals containing the cos and sin components of the fluorescent signal and the high-frequency component and outputted by the phase difference detector 126 to extract the cos and sin components of the fluorescent signal. This allows the processing unit 120 to obtain information about the phase difference of donor fluorescence with reference to the modulation signal (first phase difference).

The controller 130 controls the signal generating unit 110 so that the signal generating unit 110 generates, as a modulation signal, a sinusoidal signal according to an instruction regarding the modulation frequency from the analyzing unit 150 that will be described later. The controller 130 performs AD conversion on the cos and sin components of the fluorescent signals outputted by the signal processing unit 120.

The controller 130 includes an amplifier 134, an A/D converter 136, and a system controller 138. The amplifier 134 amplifies the processed signals containing the cos and sin components of the fluorescent signals sent from the processing unit 120, and outputs the amplified processed signals to the A/D converter 136. The A/D converter 136 samples the processed signals containing the cos and sin components of the fluorescent signals, and supplies them to the analyzing device 150. The system controller 138 receives an input of the trigger signal outputted by the measuring unit 40. The system controller 138 controls the oscillator 112 and the A/D converter 136.

The analyzing unit 150 calculates fluorescence lifetime and fluorescence intensity from the processed signals supplied from the controller 130 and containing the cos and sin components (real and imaginary parts) of the fluorescent signal of donor fluorescence and the fluorescent signal of acceptor fluorescence.

Figure 6:
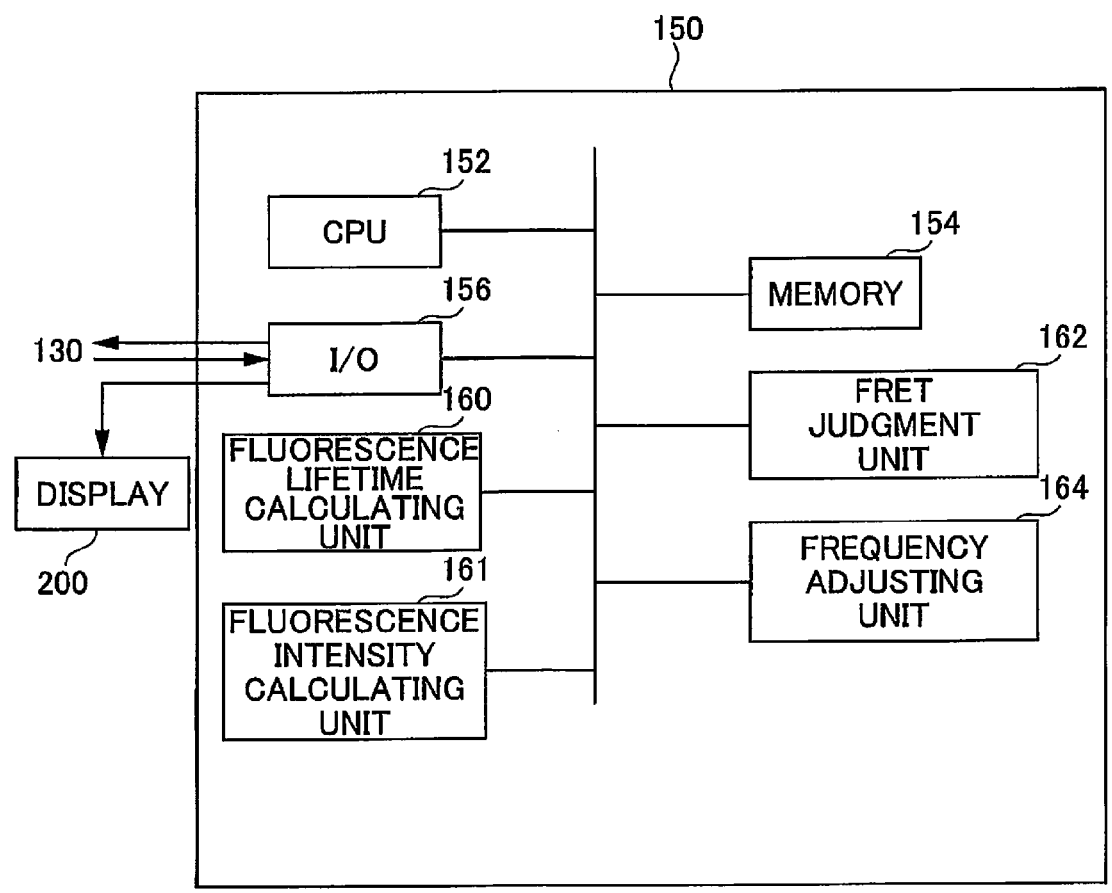
FIG. 6 is a schematic configuration diagram that illustrates one example of an analyzing unit of this embodiment.

The analyzing unit 150 is a device configured by executing a predetermined program on a computer. FIG. 6 is a schematic configuration diagram that illustrates one example of the analyzing unit 150 of this embodiment. As illustrated in FIG. 6, the analyzing unit 150 includes a CPU 152, a memory 154, and an input-output port 156. The analyzing unit 150 executes the program stored in the memory 154 to configure a fluorescence lifetime calculating unit 160, a fluorescence intensity calculating unit 161, a FRET judgment unit 162, and a frequency adjusting unit 164 as software modules.

The analyzing unit 150 is connected to a display 200 via the input-output port 156. The analyzing unit 150 is connected also to the controller 130 via the input-output port 156.

The CPU 152 is an arithmetic processor provided in the computer. The CPU 152 virtually performs various calculations of the fluorescence lifetime calculating unit 160, the fluorescence intensity calculating unit 161, the FRET judgment unit 162, and the frequency adjusting unit 164.

The memory 154 includes ROM that stores the program executed on the computer to configure the fluorescence lifetime calculating unit 160, the fluorescence intensity calculating unit 161, the FRET judgment unit 162, and the frequency adjusting unit 164 as software modules and RAM that memorizes processing results calculated by these parts and data supplied from the input-output port 156.

The input-output port 156 receives an input of values of the cos(cosine) and sin(sine) components (real and imaginary parts) of the fluorescent signals of donor fluorescence and acceptor fluorescence supplied from the controller 130. The input-output port 156 outputs processing results calculated by the various units to the display 200.

The display 200 displays a variety of information or processing results determined by the various units.

The fluorescence lifetime calculating unit 160 uses the values of cos and sin components (real and imaginary parts) of the fluorescent signal of donor fluorescence supplied from the controller 130 to calculate the fluorescence lifetime of donor fluorescence emitted from the donor fluorescent substance 2. For example, the fluorescence lifetime calculating unit 160 determines the phase difference θ of the fluorescent signal with respect to the modulation signal (first phase difference) from the values of cos and sin components of the fluorescent signal supplied from the controller 130. Further, the fluorescence lifetime calculating unit 160 uses the determined phase difference θ to calculate the fluorescence lifetime of the donor fluorescent substance 2. More specifically, the fluorescence lifetime calculating unit 160 divides, based on the formula $\tau_{sample} = -\tan \theta/(2\pi f)$, the tangent component of the phase difference θ by the angular frequency $2\pi f$ (f is a modulation frequency) of the modulation signal to acquire a fluorescence lifetime $\tau_{sample}$ of donor fluorescence of the measuring probe 1. The fluorescence lifetime $\tau_{sample}$ is expressed as a fluorescence relaxation time constant defined by assuming that the fluorescent components emitted by laser light irradiation are based on a relaxation response of first-order lag system.

The fluorescence intensity calculating unit 161 uses the input of values of cos and sin components (real and imaginary parts) of the fluorescent signal of donor fluorescence and the fluorescent signal of acceptor fluorescence supplied from the controller 130 to calculate the fluorescence intensity of donor fluorescence and the fluorescence intensity of acceptor fluorescence. More specifically, the fluorescence intensity calculating unit 161 determines the square root of the sum of squares of values of the cos component (real part) and sin component (imaginary part) of each of the fluorescent signal of donor fluorescence and the fluorescent signal of acceptor fluorescence to calculate fluorescence intensity.

The FRET judgment unit 162 uses the fluorescence lifetime $\tau_{sample}$ obtained by the fluorescence lifetime calculating unit 160, the fluorescence intensity of donor fluorescence, and the fluorescence intensity of acceptor fluorescence to judge whether or not the test object 5 has the separating property. More specifically, the FRET judgment unit 162 judges whether a set of the fluorescence lifetime $\tau_{sample}$ and a ratiometry $R_{sample}$, which is a ratio of the fluorescence intensity of acceptor fluorescence to the fluorescence intensity of donor fluorescence, falls in a set of the ranges. One of the set of the ranges is a range in which a fluorescence lifetime $\tau_{FRET}$ to be described later can take values and the other is a range in which a ratiometry $R_{FRET}$ to be described later can take values. Alternatively, one of the set of the ranges is a range in which a fluorescence lifetime $\tau_{NON-FRET}$ to be described later can take values and the other is a range in which a ratiometry $R_{NON-FRET}$ to be described later can take values. Then the FRET judgment unit 162 judges whether or not the test object 5 has the separating property. The FRET judgment unit 162 can also, of course, judge whether or not the test object 4 has the approaching/binding property when the test object 4 is given to the measuring probe 1 having the probe element X and the probe element Y that are in a state illustrated in FIG. 1A.

The FRET judgment unit 162 previously determines, by the use of the measuring probes 1, a range in which the fluorescence lifetime $\tau_{FRET}$ of donor fluorescence can take values at the time when FRET occurs and determines, by the use of the measuring probes 1, a range in which the fluorescence lifetime $\tau_{NON-FRET}$ of donor fluorescence can take values at the time when FRET does not occur. Further, the FRET judgment unit 162 previously determines a range in which the ratiometry $R_{FRET}$ that is the ratio of the fluorescence intensity of acceptor fluorescence to the fluorescence intensity of donor fluorescence (hereinafter, referred to as ratiometry) can take values at the time when FRET occurs, and determines a range in which the ratiometry $R_{NON-FRET}$ can take values at the time when FRET does not occur. The reason why such ranges in which the fluorescence lifetime or the ratiometry can take values, are set is because the values of the fluorescence lifetime and the ratiometry vary among different measuring probes 1 in FRET fluorescence measurement, and therefore the FRET judgment unit 162 needs to statistically make a judgment. For this reason, the FRET judgment unit 162 acquires a plurality of sets of the fluorescence lifetime $\tau_{sample}$ obtained by the fluorescence lifetime calculating unit 160 and the ratiometry $R_{sample}$, and determines whether each of the sets falls in the range in which the fluorescence lifetime $\tau_{FRET}$ can take values and the range in which the ratiometry $R_{FRET}$ can take values, alternatively each of the sets falls in the range in which the fluorescence lifetime $\tau_{NON-FRET}$ can take values and the range in which the ratiometry $R_{NON-FRET}$ can take values. Thereby, the presence or absence of FRET is statistically judged.

That is, the FRET judgment unit 162 uses the fluorescence lifetime $\tau_{sample}$ of donor fluorescence, the fluorescence intensity of donor fluorescence, and the fluorescence intensity of acceptor fluorescence to judge whether or not the test object 5 has the property. When the FRET judgment unit 162 judges that FRET is absent, the test object 5 illustrated in FIG. 1C is judged to have the separating property. When the FRET judgment unit 162 judges that FRET is present, the test object 5 illustrated in FIG. 1C is judged to have no separating property.

The range in which the fluorescence lifetime $\tau_{FRET}$ of donor fluorescence can take values at the time when FRET occurs, may be determined by the following method. More specifically, a positive control sample containing the measuring probe 1 is used instead of the test sample to determine, as a second phase difference, the phase difference of donor fluorescence with respect to the modulation signal measured through the flow cytometer 10. The flow cytometer 10 determines, from this second phase difference and the modulation frequency, values of the fluorescence lifetime $\tau_{FRET}$ of donor fluorescences at the time when FRET occurs, and sets a range in which the fluorescence lifetime $\tau_{FRET}$ can take values, based on the distribution of the values of the fluorescence lifetime $\tau_{FRET}$.

Further, the range in which the ratiometry $R_{FRET}$ can take values at the time when FRET occurs, may also be determined by the following method. More specifically, a positive control sample containing the measuring probe 1 is used instead of the test sample to determine values of the ratiometry $R_{FRET}$ that is the ratio of the fluorescence intensity of acceptor fluorescence to the fluorescence intensity of donor fluorescence measured through the flow cytometer 10. The flow cytometer 10 sets a range in which the ratiometry $R_{FRET}$ can take values, based on the distribution of the values of the ratiometry $R_{FRET}$. The positive control sample refers to a sample containing the measuring probe 1 whose probe element X and probe element Y are allowed to approach to each other (or bind together) so that the donor fluorescent substance 2 and the acceptor fluorescent substance 3 are located close to each other to the extent that FRET occurs. Such a positive control sample may be prepared by, for example, adding a substance known to allow the probe element X and the probe element Y to reliably approach to each other (or bind together), into a sample containing the probe element X and the probe element Y.

The range in which the fluorescence lifetime $\tau_{NON-FRET}$ of donor fluorescence can take values at the time when FRET does not occur, can also be set as in the case of the range in which the fluorescence lifetime $\tau_{FRET}$ can take. In this case, a negative control sample is used instead of the positive control sample. The range in which the ratiometry $R_{NON-FRET}$ can take values at the time when FRET does not occur, can also be set as in the case of the range in which the ratiometry $R_{FRET}$ can take values. In this case, a negative control sample is used instead of the positive control sample.

The negative control sample refers to a sample containing the measuring probe 1 whose probe element X and probe element Y are separated from each other so that the donor fluorescent substance 2 and the acceptor fluorescent substance 3 are separated from each other to the extent that FRET does not occur. A negative control sample liquid may be prepared by, for example, adding a substance known to allow the probe element X and the probe element Y to be reliably separated from each other, into a sample liquid containing the probe element X and the probe element Y.

The frequency adjusting unit 164 determines, prior to measurement of FRET by the flow cytometer 10 using the test sample containing the measuring probe 1 and the test object 5, information about an optimum modulation frequency that maximizes a difference between the phase difference of donor fluorescence with respect to the modulation signal at the time when FRET occurs in the measuring probe 1 (second phase difference) and the phase difference of donor fluorescence with respect to the modulation signal at the time when FRET does not occur in the measuring probe 1 FRET (third phase difference). Here, the optimum frequency is a frequency in the range of 50% to 200% (±1 octave) of a frequency that maximizes a difference between the second phase difference and the third phase difference. That is, the optimum frequency falls in the range of 50% to 200% of a frequency that maximizes a difference between the second phase difference and the third phase difference. The optimum frequency preferably falls in the range of 75% to 150% of a frequency that maximizes a difference between the second phase difference and the third phase difference, and more preferably falls in the range of 80% to 120% of a frequency that maximizes a difference between the second phase difference and the third phase difference. The frequency adjusting unit 164 sends the determined information about the optimum modulation frequency to the controller 130 via the input-output port 156. The controller 130 controls the signal generating unit 110 so that the signal generating unit 110 generates, as a modulation signal, a sinusoidal signal having the optimum modulation frequency according to an instruction regarding this optimum modulation frequency. Therefore, the modulation frequency for modulating the intensity of the laser light with which the measuring probe 1 is irradiated is adjusted to the optimum modulation frequency.

Such an optimum modulation frequency can be previously found out by measurement using the flow cytometer 10. Alternatively, the optimum modulation frequency may be found out based on the result of a simulation calculation. The simulation calculation is performed using the values of a fluorescence parameter including information about known fluorescence lifetime and fluorescence intensity inherent in the donor fluorescent substance 2. Thereby, the phase difference of donor fluorescence with respect to the modulation signal is determined while the modulation frequency is changed.

When the optimum modulation frequency is found out by measurement using the flow cytometer 10, a value Z to be described below is preferably determined.

More specifically, a FRET sample group containing the positive control samples in which FRET occurs is prepared, and a NON-FRET sample group containing the negative control samples in which FRET does not occur is prepared, as well.

The positive control sample is used as each of samples of the FRET sample group and measured by the flow cytometer 10. From the measurement result for each sample, the fluorescence lifetime calculating unit 160 determines the phase difference of donor fluorescence with respect to the modulation signal at the time when FRET occurs (second phase difference) or the fluorescence lifetime $\tau_{FRET}$ obtained from this phase difference. Thereby, the FRET judgment unit 162 determines an average Ave1 and standard deviation Sd1 of the second phase differences or the fluorescence lifetimes $\tau_{FRET}$ of the FRET sample group. Further, the negative control sample is used as each of samples of the NON-FRET sample group and measured by the flow cytometer 10. From the measurement result for each sample, the fluorescence lifetime calculating unit 160 determines the phase difference of donor fluorescence with respect to the modulation signal at the time when FRET does not occur (third phase difference) or the fluorescence lifetime $\tau_{NON-FRET}$ obtained from this third phase difference. Thereby, the FRET judgment unit 162 determines an average Ave2 and standard deviation Sd2 of the third phase differences or of the fluorescence lifetimes $\tau_{NON-FRET}$ of the NON-FRET sample group. At this time, a value Z determined by the following formula is preferably more than 0 but less than 1 at the optimum modulation frequency determined by the frequency adjusting unit 164.

$$Z=1-3 \cdot (Sd1+Sd2)/|Ave1-Ave2|$$

The phase difference or the fluorescence lifetime obtained in this embodiment varies. Therefore, the optimum modulation frequency having statistical reliability is preferably determined in consideration of such variations. In general, when variations in the phase difference or the fluorescence lifetime among the samples follow a normal distribution, 99.74% of all the samples are positioned in the range of average−3×standard deviation to average+3×standard deviation of the phase difference or fluorescence lifetime. Therefore, the above value Z indicates how large the distance (shortest distance) is with respect to the distance between the averages represented by |Ave1−Ave2|, in which the distance (shortest distance) is between the end of a so-called 3 sigma range containing 99.74% among values of the second phase difference or fluorescence lifetime $\tau_{FRET}$ of the FRET sample group and the end of a so-called 3 sigma range containing 99.74% among values of the third phase difference or fluorescence lifetime $\tau_{NON-FRET}$ of the NON-FRET sample group represented by |Ave1−Ave2|−3·(Sd1+Sd2). When the value Z is 1, Sd1+Sd2 is 0, which indicates that there are no variations. When the value Z is 0, the upper end (or lower end) of the 3 sigma range of the second phase difference or fluorescence lifetime $\tau_{FRET}$ of the FRET sample group and the lower end (or upper end) of the 3 sigma range of the third phase difference or fluorescence lifetime $\tau_{NON-FRET}$ overlap one another. Therefore, at the optimum frequency used in this embodiment, the value Z is preferably more than 0 but less than 1, more preferably 0.2 or more but less than 1, even more preferably 0.5 or more but less than 1.

In this way, the value Z can be used as an indicator of reliability for variations in measurement result from sample to sample. Further, as described above, since a frequency in the range of 50% to 200% of a frequency that maximizes a difference between the second phase difference and the third phase difference is set as the optimum frequency, the optimum frequency is preferably selected from such a range so that the value Z is larger.

The reason why the flow cytometer 10 uses the optimum modulation frequency that maximizes a difference between the second phase difference and the third phase difference as a modulation frequency for modulating the intensity of the laser light is to reduce errors in judgment as to the presence or absence of FRET. Particularly, when donor fluorescence contains two or more kinds of fluorescent components different in fluorescence lifetime, the calculated value of the fluorescence lifetime $\tau_{sample}$ is often higher than the actual value. Therefore, there is a case where it is difficult to find out the presence or absence of the occurrence of FRET based on a change in the value of the fluorescence lifetime $\tau_{sample}$. In general, the value of fluorescence lifetime $\tau_{FRET}$ of donor fluorescence is reduced when FRET occurs, and therefore, it can be judged that FRET has occurred based on a reduction in the value of the fluorescence lifetime $\tau_{sample}$. However, when donor fluorescence contains two or more kinds of fluorescent components different in fluorescence lifetime, a change in the calculated value of the fluorescence lifetime $\tau_{sample}$ is smaller than a change in the value of the fluorescence lifetime $\tau_{sample}$ which is calculated when donor fluorescence contains only a single fluorescent component having one fluorescence lifetime even when FRET occurs. Therefore, there is a case where it is difficult to judge that FRET has occurred based on a reduction in the value of the fluorescence lifetime $\tau_{sample}$. For this reason, the flow cytometer 10 uses, as a modulation frequency for modulating the intensity of the laser light, the optimum modulation frequency that maximizes a difference between the second phase difference and the third phase difference to obtain a major change of the fluorescence $\tau_{sample}$ between the presence of FRET and the absence of FRET. Therefore, the flow cytometer 10 can accurately judge the presence or absence of the occurrence of FRET.

Figure 7A:
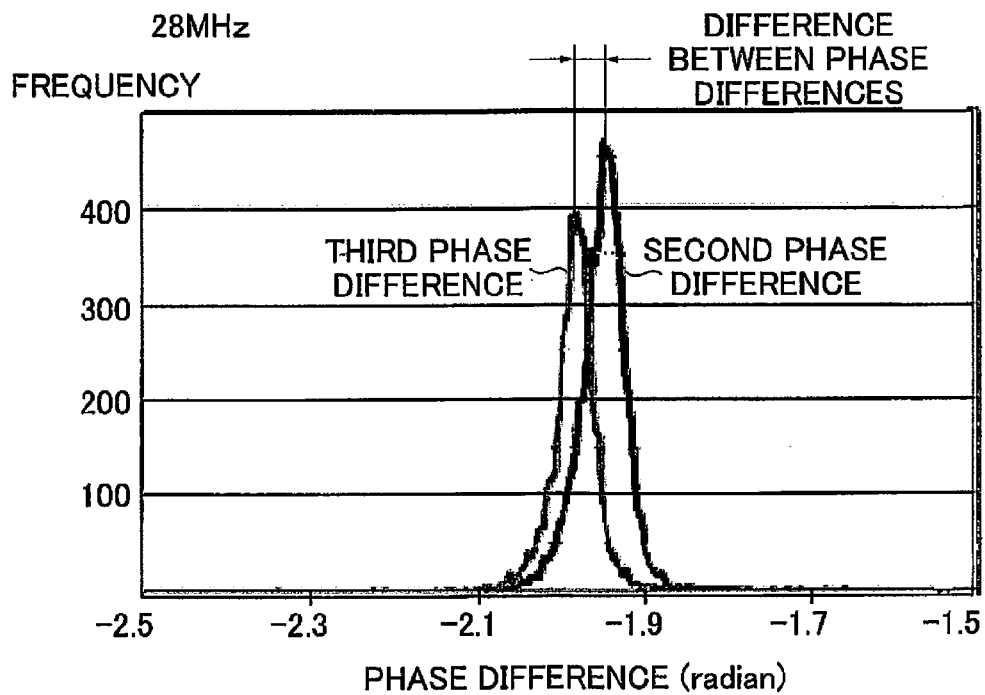
FIG. 7A illustrates one example of a phase difference frequency diagram measured by the flow cytometer according to this embodiment at a modulation frequency of 28 MHz.
Figure 7B:
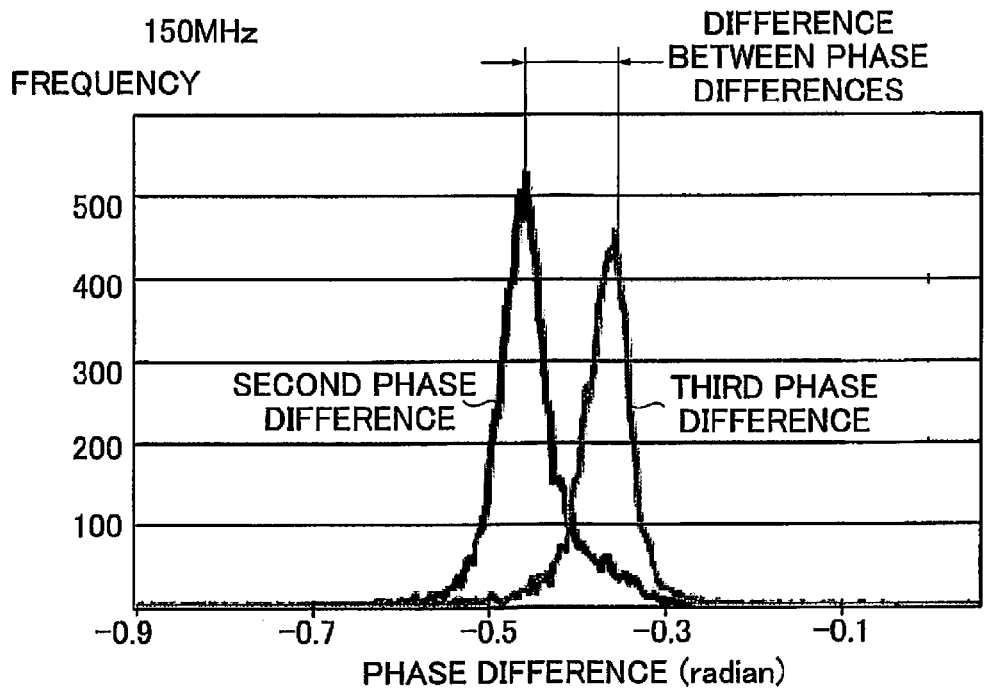
FIG. 7B illustrates one example of a phase difference frequency diagram measured by the flow cytometer according to this embodiment at a modulation frequency of 150 MHz.

FIG. 7A is a phase difference frequency diagram measured by the flow cytometer 10 at a modulation frequency of 28 MHz. FIG. 7B is a phase difference frequency diagram measured by the flow cytometer 10 at a modulation frequency of 150 MHz. The second phase difference in each of FIGS. 7A and B represents a phase difference at the time when the positive control sample containing the measuring probe 1 is used. The third phase difference in each of FIGS. 7A and B represents a phase difference at the time when the negative control sample containing the measuring probe 1 is used.

As illustrated in FIG. 7A, a difference between the second phase difference and the third phase difference at the greatest frequency at the time when the modulation frequency is set to 28 MHz is about 0.04 radian. On the other hand, as illustrated in FIG. 7B, a difference between the second phase difference and the third phase difference at the greatest frequency at the time when the modulation frequency is set to 150 MHz is about 0.10 radian. As can be seen from the above, a difference between the second phase difference and the third phase difference varies depending on the modulation frequency.

Figures 8A, 8B:
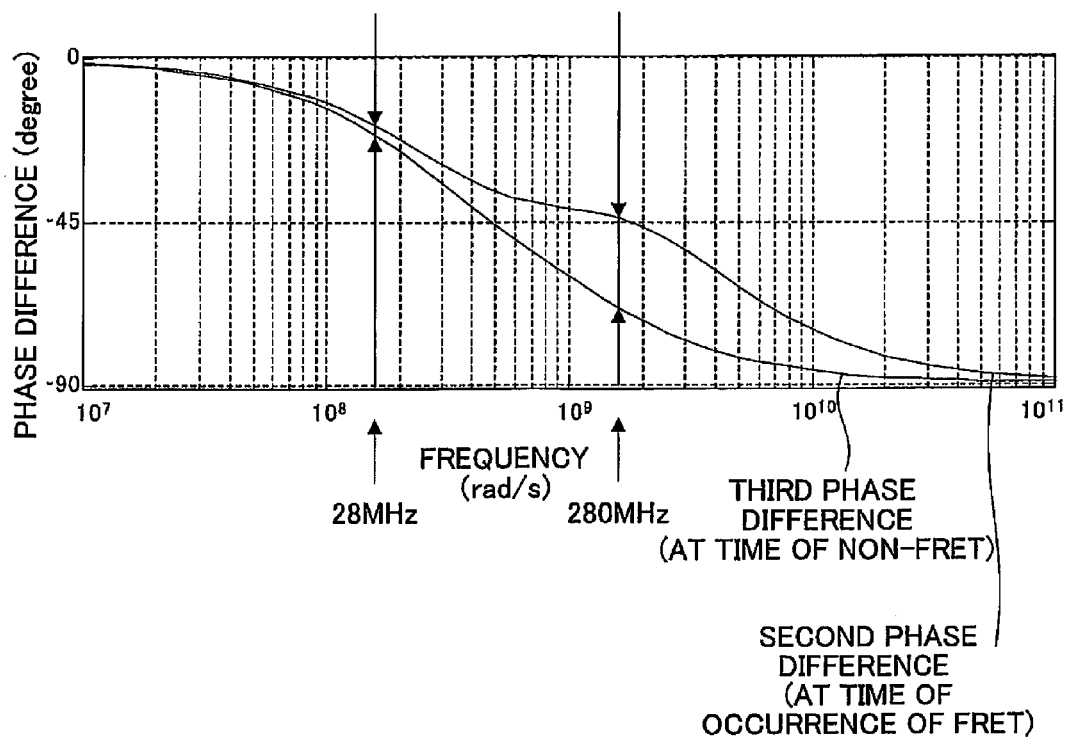
FIG. 8A illustrates examples of fluorescence parameters of donor fluorescence identified by measurement using known fluorescence lifetime imaging microscopy.
FIG. 8B is a diagram that illustrates examples of frequency characteristics of a second phase difference and a third phase difference obtained by a simulation calculation using values of the fluorescence parameters illustrated in FIG. 8A.

FIG. 8A illustrates examples of values of fluorescence parameters of donor fluorescence measured using known fluorescence lifetime imaging microscopy. The values of the fluorescence parameters are identified by assuming that donor fluorescence emitted from the donor fluorescent substance 2 is a relaxation response of first-order lag system. The donor fluorescence has two kinds of fluorescent components (first fluorescent component, second fluorescent component) different in fluorescence lifetime. In this case, FRET occurs in the second fluorescent component so that a fluorescence lifetime $\tau_2$ of the second fluorescent component is significantly reduced from 1.0 (nanosecond) to 0.3 (nanosecond). The fluorescence lifetime imaging microscopy is disclosed in, for example, "Multiple frequency fluorescence lifetime imaging microscopy" A. SQUIRE et al., Journal of Microscopy, vol. 197, Pt2, February 2000, pp. 136-149.

Here, $\alpha_i$ (i=1 or 2) represents a relative ratio of the fluorescence intensity of the first or second fluorescent component. Therefore, the fluorescence intensity of the first fluorescent component is expressed as $\alpha_1 \times \exp(-t/\tau_1)$, and the fluorescence intensity of the second fluorescent component is expressed as $\alpha_2 \times \exp(-t/\tau_2)$.

A temporal change in such donor fluorescence intensity is measured using known fluorescence lifetime imaging microscopy, and the measured time response of fluorescence intensity of donor fluorescence is curve-fitted to the formula $\alpha_1 \times \exp(-t/\tau_1) + \alpha_2 \times \exp(-t/\tau_2)$, which makes it possible to calculate the values of $\alpha_1$, $\tau_1$, $\alpha_2$, and $\tau_2$. FIG. 8A illustrates the known values of the fluorescence parameters acquired in this way. Therefore, changes in the second phase difference and the third phase difference with respect to the modulation frequency can be calculated using the values of these fluorescence parameters. More specifically, the phase difference with respect to the modulation frequency f can be calculated according to the following formula (1).

[Formula 1]

$$\text{Phase difference} = \arg\left(\frac{\alpha_1 \tau_1}{1 + j2\pi f \tau_1} + \frac{\alpha_2 \tau_2}{1 + j2\pi f \tau_2}\right) \quad (1)$$

(j is an imaginary unit, f is a modulation frequency)

The values of such fluorescence parameters for each kind of the donor fluorescent substance 2 and the acceptor fluorescent substance 3 are previously stored in the memory 154. The frequency adjusting unit 164 can call the values of the fluorescence parameters from the memory 154 depending on the kinds of the donor fluorescent substance 2 and the acceptor fluorescent substance 3 used in the measuring probe 1 to calculate the phase difference with respect to the modulation frequency f.

FIG. 8B illustrates examples of the second phase difference and the third phase difference calculated according to the above formula (1). In this case, a difference between the second phase difference and the third phase difference is maximized at a frequency of 280 MHz. Therefore, when a fluorescent substance, which emits two or more kinds of fluorescent components, each having known values of a fluorescence parameter including information about fluorescence lifetime and fluorescence intensity, is used as the donor fluorescent substance 2, the frequency adjusting unit 164 can calculate the second phase difference and the third phase difference using the values of the fluorescence parameter while changing the modulation frequency, and find out, based on the result of the calculation, the optimum modulation frequency that maximizes a difference between the second phase difference and the third phase difference.

It is to be noted that, when donor fluorescence has the first fluorescent component and the second fluorescent component illustrated in FIG. 8A, an average fluorescence lifetime $\tau_{AVE}$ is determined as the fluorescence lifetime $\tau_{sample}$ according to the following formula by measurement using the flow cytometer 10.

Average fluorescence lifetime $\tau_{AVE} = f_1 \cdot \tau_1 + f_2 \cdot \tau_2$ Here, $f_1$ is expressed as $\alpha_1 \cdot \tau_1 / (\alpha_1 \cdot \tau_1 + \alpha_2 \cdot \tau_2)$, and $f_2$ is expressed as $\alpha_2 \cdot \tau_2 / (\alpha_1 \cdot \tau_1 + \alpha_2 \cdot \tau_2)$.

Therefore, in the case of the example illustrated in FIG. 8A, the average fluorescence lifetime $\tau_{AVE}$ determined by measurement using the flow cytometer 10 at the time of NON-FRET is 2.5 (n sec) and that at the time of the occurrence of FRET is 2.23 (n sec). In this case, even when the fluorescence lifetime $\tau_2$ of the second fluorescent component changes from 1.0 (n sec) to 0.3 (n sec) due to the occurrence of FRET, the fluorescence lifetime measured by the flow cytometer 10 only slightly changes from 2.5 (n sec) to 2.23 (n sec), that is, the amount of a change in the fluorescence lifetime is small. In this embodiment, in order to increase the amount of a change in the fluorescence lifetime that only slightly changes, the modulation frequency at which the intensity of the laser light is modulated is adjusted to the above-described optimum modulation frequency.

As described above, in this embodiment, the modulation frequency used to modulate the intensity of the laser light is adjusted to the optimum modulation frequency that maximizes a difference between the second phase difference of donor fluorescence with respect to the modulation signal at the time when FRET occurs and the third phase difference of donor fluorescence with respect to the modulation signal at the time when no FRET occurs. Therefore, it is possible to accurately judge the presence or absence of the occurrence of FRET. Particularly, the use of the flow cytometer allows short-time measurement, which makes it possible to determine whether or not the test object has the separating property or the approaching/binding property in a shorter time as compared to when the conventional fluorescence lifetime imaging microscopy is used.

Further, in this embodiment, the phase differences of donor fluorescence with respect to the modulation signal (phase difference at the time of the occurrence of FRET and phase difference at the time of NON-FRET) are determined by measuring the positive control sample and the negative control sample with the use of the flow cytometer 10, respectively, and the optimum modulation frequency for the flow cytometer 10 is found out based on a difference between the determined two phase differences. Therefore, the flow cytometer 10 can more accurately judge the presence or absence of the occurrence of FRET by using the test sample and then judge whether or not the test object has the separating property or the approaching/binding property.

Alternatively, the frequency adjusting unit 164 calculates the phase differences of donor fluorescence with respect to the modulation signal (phase difference at the time of NON-FRET and phase difference at the time of the occurrence of FRET) by using the fluorescence parameter of the measuring probe 1 while changing the modulation frequency, and finds out the optimum modulation frequency based on the result of this calculation. Therefore, the optimum frequency can be simply acquired by calculation without previously performing measurement using the flow cytometer 10.

Further, in this embodiment, a range in which the fluorescence lifetime $\tau_{FRET}$ of donor fluorescence of the measuring probe 1 can take values, a range in which the fluorescence lifetime $\tau_{NON-FRET}$ of donor fluorescence can take values at the time when no FRET occurs, a range in which the ratiometry $R_{FRET}$ can take values at the time when FRET occurs, and a range in which the ratiometry $R_{NON-FRET}$ can take values at the time when no FRET occurs, are previously acquired. The FRET judgment unit 162 uses these ranges for judgment, and therefore can more accurately judge whether or not the test object 5 has the property.

It is to be noted, since the range in which the fluorescence lifetime $\tau_{FRET}$ can take values, the range in which the fluorescence lifetime $\tau_{NON-FRET}$ can take values, the range which the ratiometry $R_{FRET}$ can take values, the range in which the ratiometry $R_{NON-FRET}$ can take values are acquired by measuring the positive control sample containing the measuring probe 1 and the negative control sample containing the measuring probe 1 with the use of the flow cytometer 10, the property of the test object 5, which is measured by the same flow cytometer 10, can be more accurately judged.

<FRET Measurement Method>

Figure 9:
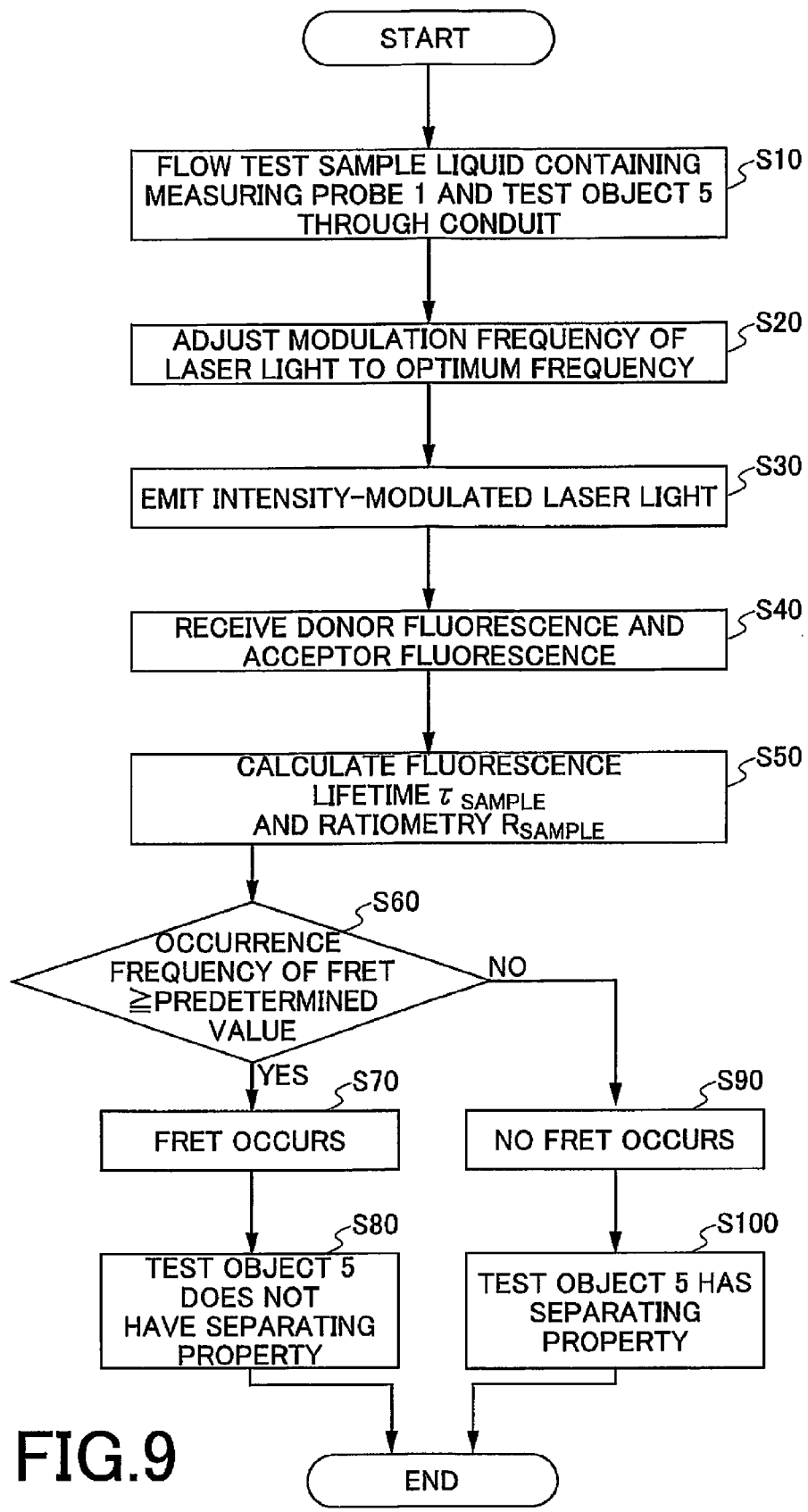
FIG. 9 is a diagram that illustrates the flow of one example of a FRET measurement method according to this embodiment.

FIG. 9 is a diagram that illustrates the flow of one example of the FRET measurement method according to this embodiment.

The flow illustrated in FIG. 9 will be described with reference to a case where a judgment is made as to whether or not the test object 5 has such a property as illustrated in FIG. 1C, that is, whether or not the test object 5 has the separating property when the test object 5 is given to the measuring probe 1 being in a state illustrated in FIG. 1B.

First, as illustrated in FIG. 1B, the measuring probe 1 is prepared which is in a state where the probe element X and the probe element Y approach to each other (or bind together) so that the donor fluorescent substance 2 and the acceptor fluorescent substance 3 are located close to each other and FRET occurs. A test sample containing this measuring probe 1 and the test object 5 is prepared and flowed through the conduit 20 of the flow cytometer 10 (Step S10).

On the other hand, the frequency adjusting unit 164 of the analyzing unit 150 of the flow cytometer 10 finds out an optimum modulation frequency that maximizes a difference between the phase difference of donor fluorescence with respect to the modulation signal at the time when FRET occurs in the measuring probe 1 (second phase difference) and the phase difference of donor fluorescence with respect to the modulation signal at the time when FRET does not occur in the measuring probe 1 (third phase difference), and sends information about this optimum modulation frequency to the controller 130. The controller 130 givens an instruction to the oscillator 112 to generate a modulation signal having the optimum modulation frequency. This allows the flow cytometer 10 to adjust the modulation frequency of laser light to the optimum modulation frequency (Step S20).

The optimum frequency is preferably found out by actually measuring fluorescence with the flow cytometer 10 by using a positive control sample and a negative control sample while changing the modulation frequency. In this case, the frequency adjusting unit 164 obtains, as a second phase difference and a third phase difference, the phase differences of donor fluorescence emitted from the donor fluorescent substance with respect to the modulation signal by using the flow cytometer 10, and finds out the optimum modulation frequency based on the difference between the second phase difference and the third phase difference. At this time, averages and standard deviations may be determined by measuring a FRET sample group containing the positive control samples and a NON-FRET sample group containing the negative control samples to determine the above-described value Z as an indicator of the reliability of measurement at the optimum frequency. In this case, the value Z at the optimum modulation frequency is preferably more than 0 but less than 1.

Alternatively, when the donor fluorescent substance emits two or more kinds of fluorescent components, each having known values of a fluorescence parameter including information about fluorescence lifetime and fluorescence intensity, the frequency adjusting unit 164 may preferably perform a simulation calculation using the values of the fluorescence parameter while changing the modulation frequency to determine the phase differences of donor fluorescence with respect to the modulation signal (the above-described second and third phase differences), and find out the optimum modulation frequency based on the result of this simulation calculation. The values of the fluorescence parameter are preferably identified by, for example, using fluorescence lifetime imaging microscopy.

The light source unit 30 modulates intensity based on the modulation signal having the optimum modulation frequency. Therefore, the light source unit 30 emits laser light whose intensity is modulated at the optimum modulation frequency toward the conduit 20 (Step S30).

The light-receiving unit 50 receives donor fluorescence and acceptor fluorescence emitted from the donor fluorescent substance 2 and the acceptor fluorescent substance 3 of the measuring probe 1 contained in the test sample by irradiation with the intensity-modulated laser light, and outputs fluorescent signals (Step S40).

The signal processing unit 120 processes the fluorescent signals outputted by the light-receiving unit 50 to generate cos and sin components of the fluorescent signals. That is, the signal processing unit 120 generates information about the phase difference of donor fluorescence emitted from the measuring probe 1 with respect to the modulation signal (first phase difference).

Further, the fluorescence lifetime calculating unit 160 of the analyzing unit 150 determines, using the cos and sin components of the fluorescent signal, the phase difference of donor fluorescence with respect to the modulation signal (first phase difference), and acquires a fluorescence lifetime $\tau_{SAMPLE}$ of donor fluorescence calculated from the phase difference. Further, the fluorescence intensity calculating unit 161 of the analyzing unit 150 calculates the fluorescence intensity of donor fluorescence and the fluorescence intensity of acceptor fluorescence. Then, the analyzing unit 150 calculates a ratiometry $R_{SAMPLE}$ of the acceptor fluorescence intensity to the donor fluorescence intensity. That is, the analyzing unit 150 calculates the fluorescence lifetime $\tau_{SAMPLE}$ of donor fluorescence and the ratiometry $R_{SAMPLE}$ (Step S50). In this embodiment, the fluorescence lifetime $\tau_{SAMPLE}$ and the ratiometry $R_{SAMPLE}$ are calculated every time the measuring probe 1 contained in the test sample passing through the measuring point in the conduit 20 is irradiated with the laser light, and therefore a very large amount of data of the fluorescence lifetime $\tau_{SAMPLE}$ and the ratio $R_{SAMPLE}$ is obtained when measurement of the measuring probe 1 of all the test sample is finished. Therefore, the analyzing unit 150 statistically judges the occurrence of FRET with the large amount of data about the fluorescence lifetime $\tau_{SAMPLE}$ and the ratio $R_{SAMPLE}$. That is, the FRET judgment unit 162 judges whether or not the occurrence probability (%) of FRET is equal to or higher than a predetermined value (Step S60).

More specifically, a plurality of values of the fluorescence lifetime $\tau_{SAMPLE}$ and a plurality of values of the ratiometry $R_{SAMPLE}$ are acquired as data by using the test sample. The occurrence probability (%) of FRET refers to the ratio of the amount of the data contained in a preset range in which a fluorescence lifetime $\tau_{FRET}$ can take values and a preset range in which a ratiometry $R_{FRET}$ can take values, to the amount of all the data. Further, in order to make a judgment more reliably, an additional judgment is preferably made as to whether or not the ratio of the amount of the data of values of the fluorescence lifetime $\tau_{SAMPLE}$ and values of the ratiometry $R_{SAMPLE}$ contained in a preset range of a fluorescence lifetime $\tau_{NON-FRET}$ and a preset range of a ratiometry $R_{NON-FRET}$, to the amount of all the data, is higher than a preset value.

The four ranges, i.e., the range in which the fluorescence lifetime $\tau_{FRET}$ can take values, the range in which the ratiometry $R_{FRET}$ can take values, the range in which the fluorescence lifetime $\tau_{NON-FRET}$ can take values, and the range in which the ratiometry $R_{NON-FRET}$ can take values are preferably set by previously measuring the fluorescence lifetime of donor fluorescence, the fluorescence intensity of donor fluorescence, and the fluorescence intensity of acceptor fluorescence by using the positive control sample and the negative control sample in the flow cytometer 10.

When the judgment result is YES, the FRET judgment unit 162 judges that FRET occurs in the measuring probe 1 (Step S70) and that the test object 5 does not have the property of separating the probe element X and the probe element Y of the measuring probe 1 from each other (Step S80). On the other hand, when the judgment result is NO, the FRET judgment unit 162 judges that FRET does not occur in the measuring probe 1 (Step S90) and that the test object 5 has the property of separating the probe element X and the probe element Y of the measuring probe 1 from each other (Step S100). This judgment result is outputted to the display 200.

In this way, the flow cytometer 10 can judge in a short time whether or not the test object 5 has the property of separating the measuring probe 1.

The FRET measurement method according to this embodiment can be suitably used for development of a test for the sensitivity of a molecularly-targeted drug for leukemia. Chronic myelocytic leukemia (CML) is a chronic myeloproliferative disorder that occurs due to production of an abnormal protein (BCR-ABL) in cells caused by a genetic abnormality (translocation of chromosome 9 and 22). For example, as the probe element X and the probe element Y of the measuring probe 1, a reagent for detecting tyrosine kinase activity of BCR-ABL is used. This reagent is composed of a substrate protein that is to be phosphorylated or its peptide fragment having a site to be phosphorylated by BCR-ABL, each of which is modified with two or more kinds of molecules capable of FRET occurrence. This reagent is linked to, for example, a fluorescent protein selected from the group consisting of GFP, eGFP, YFP, CFP, and DsRed and variants thereof. Screening of a tyrosine kinase inhibitor as the test object 5 can be efficiently performed by judging the presence or absence of FRET by the FRET measurement method according to this embodiment using this reagent. Such a reagent is described in JP 2009-278942 A.

The FRET measurement device and FRET measurement method according to the present invention have been described above in detail, but the present invention is not limited to the above embodiment and examples, and it should be understood that various changes and modifications may be made without departing from the scope of the present invention.

REFERENCE SIGNS LIST

1 Measuring probe
2 Donor fluorescent substance
3 Acceptor fluorescent substance
4, 5 Test object
10 Flow cytometer
20 Conduit
22 Collection container
30 Light source unit
40, 50 Light-receiving unit
51 Lens system
52 Dichroic mirror
53, 54 Band-pass filter
55, 56 Photoelectric converter
100 Control and processing unit
110 Signal generating unit
112 Oscillator
114 Powder splitter
116, 118 Amplifier
120 Signal processing unit
122, 124 Amplifier
126 Phase difference detector
128 Low-pass filter
130 Controller
134 Amplifier
136 A/D converter
138 System controller
150 Analyzing device
152 CPU
154 Memory
156 Input-output port
160 Fluorescence lifetime calculating unit
161 Fluorescence intensity calculating unit
162 FRET judgment unit
164 Frequency adjusting unit
200 Display
X, Y Probe element

The invention claimed is:

1. A FRET measurement device comprising:
   a conduit through which a test sample flows, the test sample comprising: a FRET probe that includes a probe element X labeled with a donor fluorescent substance and a probe element Y labeled with an acceptor fluorescent substance and enables FRET to occur when the probe element X and the probe element Y approach to each other or bind together; and a test object about which it is unknown whether or not it has an approaching/binding property of allowing the probe element X and the probe element Y to approach to each other or bind together or a separating property of separating the probe element X and the probe element Y that are in a state where they adjoin each other or bind together;
   a light source unit configured to emit, toward the conduit, laser light whose intensity is modulated using a modulation signal;
   a light-receiving unit configured to receive fluorescence emitted from the FRET probe in the test sample by irradiation with the intensity-modulated laser light and outputs a fluorescent signal; and
   an analyzing unit configured to: determine, using the fluorescent signal and the modulation signal, a phase difference of donor fluorescence emitted from the donor fluorescent substance with respect to the modulation signal as a first phase difference;
      further determine a fluorescence intensity of donor fluorescence emitted from the donor fluorescent substance and a fluorescence intensity of acceptor fluorescence emitted from the acceptor fluorescent substance; and
      judge, using a fluorescence lifetime of the donor fluorescence obtained from the determined first phase difference, the fluorescence intensity of donor fluorescence, and the fluorescence intensity of acceptor fluorescence, whether or not the test object has the approaching/binding property or the separating property,
   a modulation frequency used for the modulation signal in the light source unit being an optimum modulation frequency that maximizes a difference between a second phase difference of donor fluorescence emitted from the donor fluorescent substance with respect to the modulation signal at a time when the FRET occurs and a third phase difference of donor fluorescence emitted from the donor fluorescent substance with respect to the modulation signal at a time when the FRET does not occur.

2. The FRET measurement device according to claim 1, further comprising a frequency adjusting unit configured to adjust the modulation frequency, wherein
   the frequency adjusting unit is configured to:
   determine, as the second phase difference, a phase difference of donor fluorescence emitted from the donor fluorescent substance with respect to the modulation signal, by using a positive control sample containing the FRET probe whose probe element X and probe element Y are allowed to approach to each other or bind together instead of the test sample through the conduit, the light source unit, the light-receiving unit, and the analyzing unit while the modulation frequency is changed; further determine, as the third phase difference, a phase difference of donor fluorescence emitted from the donor fluorescent substance with respect to the modulation signal, by using a negative control sample containing the FRET probe whose probe element X and probe element Y are not allowed to approach to each other or bind together instead of the test sample through the conduit, the light source unit, the light-receiving unit, and the analyzing unit while the modulation frequency is changed; and
   find out the optimum modulation frequency based on a difference between the second phase difference and the third phase difference.

3. The FRET measurement device according to claim 2, wherein the positive control sample is used as each of samples of a FRET sample group that enables FRET occurrence to determine the second phase difference or a fluorescence lifetime FRET obtained from the second phase difference and then to determine an average Ave1 and standard deviation Sd1 of the second phase difference or fluorescence lifetime $\tau_{FRET}$ of the FRET sample group, and
   the negative control sample is used as each of samples of a NON-FRET sample group that does not allow FRET occurrence, to determine the third phase difference or a fluorescence lifetime $\tau_{NON\text{-}FRET}$ obtained from the third phase difference and then to determine an average Ave2 and standard deviation Sd2 of the third phase difference or fluorescence lifetime $\tau_{NON\text{-}FRET}$ of the NON-FRET sample group, then a value Z defined by the following formula at the optimum modulation frequency is more than 0 but less than 1:

$$Z=1-3\cdot(Sd1+Sd2)/|Ave1-Ave2|.$$

4. The FRET measurement device according to claim 1, wherein the donor fluorescent substance emits two or more kinds of fluorescent components, each having known values of a fluorescence parameter including information about fluorescence lifetime and fluorescence intensity, the FRET measurement device further comprising a frequency adjusting unit configured to adjust the modulation frequency, wherein the frequency adjusting unit is configured: perform a simulation calculation using the values of the fluorescence parameter while changing the modulation frequency to determine the second phase difference and third phase difference of the donor fluorescence with respect to the modulation signal; and find out the optimum modulation frequency based on a result of the simulation calculation.

5. The FRET measurement device according to claim 4, wherein the values of the fluorescence parameter are identified using fluorescence lifetime imaging microscopy.

6. The FRET measurement device according to claim 1, wherein the analyzing unit is:

previously configured to:
acquire, using the FRET probe, a range in which a fluorescence lifetime $\tau_{FRET}$ of donor fluorescence emitted from the donor fluorescent substance can take values at a time when the FRET occurs, a range in which a fluorescence lifetime $\tau_{NON\text{-}FRET}$ of the donor fluorescence emitted from the donor fluorescent substance can take values at a time when the FRET does not occur, a range in which a ratio $R_{FRET}$ of fluorescence intensity of acceptor fluorescence emitted from the acceptor fluorescent substance to fluorescence intensity of donor fluorescence emitted from the donor fluorescent substance can take values at a time when the FRET occurs, and a range in which a ratio $R_{NON\text{-}FRET}$ of fluorescence intensity of acceptor fluorescence emitted from the acceptor fluorescent substance to fluorescence intensity of donor fluorescence emitted from the donor fluorescent substance can take values at a time when the FRET does not occur;

calculate, using the first phase difference determined using the test sample and the optimum modulation frequency, a fluorescence lifetime $\tau_{sample}$ of donor fluorescence emitted from the donor fluorescent substance, and further calculate a ratio $R_{sample}$ of fluorescence intensity of acceptor fluorescence emitted from the acceptor fluorescent substance to fluorescence intensity of donor fluorescence emitted from the donor fluorescent substance; and judge, from the calculated fluorescence lifetime $\tau_{sample}$ and fluorescence intensity ratio $R_{sample}$, whether or not the test object has the approaching/binding property or the separating property based on the range in which the fluorescence lifetime $\tau_{FRET}$ can take values, the range in which the fluorescence lifetime $\tau_{NON\text{-}FRET}$ can take values, the range in which the ratio $R_{FRET}$ can take values, and the range in which the ratio $R_{NON\text{-}FRET}$ can take values.

7. The FRET measurement device according to claim 6, wherein the analyzing unit is configured to:

determine, as the second phase difference, a phase difference of donor fluorescence emitted from the donor fluorescent substance with respect to the modulation signal, by using a positive control sample containing the FRET probe whose probe element X and probe element Y are allowed to approach to each other or bind together instead of the test sample through the conduit, the light source unit, the light-receiving unit, and the analyzing unit, and to obtain, from the second phase difference and the modulation frequency, a plurality of values of the fluorescence lifetime $\tau_{FRET}$ of donor fluorescence emitted from the donor fluorescent substance at a time when the FRET occurs;

determines a plurality of values of the ratio $R_{FRET}$ from a fluorescence intensity of donor fluorescence emitted from the donor fluorescent substance and a fluorescence intensity of acceptor fluorescence emitted from the acceptor fluorescent substance, by using the positive control sample instead of the test sample through the conduit, the light source unit, the light-receiving unit;

determine the range in which the fluorescence lifetime $\tau_{FRET}$ can take values and the range in which the ratio $R_{FRET}$ can take values;

determine, as the third phase difference, a phase difference of donor fluorescence emitted from the donor fluorescent substance with respect to the modulation signal, by using a negative control sample containing the FRET probe whose probe element X and probe element Y are not allowed to approach to each other or bind together instead of the test sample through the conduit, the light source unit, the light-receiving unit, to obtain, from the third phase difference and the modulation frequency, a plurality of values of the fluorescence relaxation lifetime $\tau_{NON\text{-}FRET}$ of donor fluorescence emitted from the donor fluorescent substance at a time when the FRET does not occur; and further determine a plurality of values of the ratio $R_{NON\text{-}FRET}$ from a fluorescence intensity of the donor fluorescence and a fluorescence intensity of acceptor fluorescence emitted from the acceptor fluorescent substance, by using the negative control sample instead of the test sample through the conduit, the light source unit, the light-receiving unit, and determine the range in which the fluorescence lifetime $\tau_{NON\text{-}FRET}$ can take values and the range in which the ratio $R_{NON\text{-}FRET}$ can take values.

8. A FRET measurement method using a device comprising a conduit, a light source unit, a light-receiving unit, and an analyzing unit, the method comprising the steps of:

flowing, through the conduit, a test sample comprising: a FRET probe that comprises a probe element X containing a donor fluorescent substance and a probe element Y containing an acceptor fluorescent substance and enables FRET to occur when the probe element X and the probe element Y approach to each other or bind together; and a test object about which it is unknown whether or not it has a property of allowing the probe element X and the probe element Y to approach to each other or bind together or a property of separating from each other the probe element X and the probe element Y that are in a state where they adjoin each other or bind together;

causing the light source unit to emit laser light whose intensity is modulated using a modulation signal toward the conduit;

causing the light-receiving unit to receive fluorescence emitted from the FRET probe in the test sample by irradiation with the intensity-modulated laser light and output a fluorescent signal; and causing the analyzing unit to determine, using the fluorescent signal and the modulation signal, a phase difference of donor fluorescence emitted from the donor fluorescent substance with respect to the modulation signal as a first phase difference, further to determine a fluorescence intensity of donor fluorescence emitted from the donor fluorescent substance and a fluorescence intensity of acceptor fluorescence emitted from the acceptor fluorescent substance, and then to judge, using a fluorescence lifetime of the donor fluorescence obtained from the determined first phase difference, the fluorescence intensity of donor fluorescence, and the fluorescence intensity of acceptor fluorescence, whether or not the test object has a property of allowing the probe element X and the probe element Y to approach to each other or bind together or a property of separating the probe element X and the probe element Y from each other, a modulation frequency used for the modulation signal for intensity modulation of the laser light being an optimum modulation frequency that maximizes a difference between a second phase difference of donor fluorescence emitted from the donor fluorescent substance with respect to the modulation signal at a time when the FRET occurs and a third phase difference of donor fluorescence emitted from the donor fluorescent substance with respect to the modulation signal at a time when the FRET does not occur.

9. The FRET measurement method according to claim 8, further comprising the step of adjusting the modulation frequency, wherein when the modulation frequency is adjusted, a phase difference of donor fluorescence emitted from the donor fluorescent substance with respect to the modulation signal is determined as the second phase difference, by using a positive control sample containing the FRET probe whose probe element X and probe element Y are allowed to approach to each other or bind together instead of the test sample through the conduit, the light source unit, the light-receiving unit, and the analyzing unit while the modulation frequency is changed, a phase difference of donor fluorescence emitted from the donor fluorescent substance with respect to the modulation signal is further determined as the third phase difference, by using a negative control sample containing the FRET probe whose probe element X and probe element Y are not allowed to approach to each other or bind together instead of the test sample through the conduit, the light source unit, the light-receiving unit, and the analyzing unit while the modulation frequency is changed, and the optimum modulation frequency is found out based on a difference between the second phase difference and the third phase difference.

10. The FRET measurement method according to claim 9, wherein the second phase difference or a fluorescence lifetime $\tau_{FRET}$ obtained from the second phase difference is determined using the positive control sample as each of samples of a FRET sample group that enables FRET to occur, so that an average Ave1 and standard deviation Sd1 of the second phase difference or fluorescence lifetime $T_{FRET}$ of the FRET sample group are determined, and the third phase difference or a fluorescence lifetime $\tau_{NON-FRET}$ obtained from the third phase difference is further determined using the negative control sample as each of samples of a NON-FRET sample group that does not allow FRET to occur, so that an average Ave2 and standard deviation Sd2 of the third phase difference or fluorescence lifetime $\tau_{NON-FRET}$ of the NON-FRET sample group are determined, and then a value Z defined by the following formula at the optimum modulation frequency is more than 0 but less than 1:

$$Z=1-3\cdot(Sd1+Sd2)/|Ave1-Ave2|.$$

11. The FRET measurement method according to claim 10, wherein the values of the fluorescence parameter are identified using fluorescence lifetime imaging microscopy.

12. The FRET measurement method according to claim 8, wherein the donor fluorescent substance emits two or more kinds of fluorescent components, each having known values of a fluorescence parameter including information about fluorescence lifetime and fluorescence intensity, the FRET measurement method further comprising the step of adjusting the modulation frequency, wherein when the modulation frequency is adjusted, a simulation calculation is performed using the values of the fluorescence parameter while the modulation frequency is changed, to determine the second phase difference and third phase difference of the donor fluorescence with respect to the modulation signal, and the optimum modulation frequency is found out based on a result of the simulation calculation.

* * * * *